US005633260A

United States Patent [19]
Hausheer et al.

[11] Patent Number: 5,633,260
[45] Date of Patent: May 27, 1997

[54] 11,7 SUBSTITUTED CAMPTOTHECIN DERIVATIVES AND FORMULATIONS OF 11, 7 SUBSTITUTED CAMPTOTHECIN DERIVATIVES AND METHODS FOR USES THEREOF

[75] Inventors: Frederick H. Hausheer, San Antonio; Kochat Haridas, Houston, both of Tex.

[73] Assignee: BioNumerik Pharmaceuticals, Inc., San Antonio, Tex.

[21] Appl. No.: 518,644

[22] Filed: Aug. 24, 1995

Related U.S. Application Data

[62] Division of Ser. No. 229,527, Apr. 19, 1994, Pat. No. 5,468,754.

[51] Int. Cl.$^6$ .................................................. A61K 31/475
[52] U.S. Cl. ................................................................ 514/283
[58] Field of Search ................................................ 514/283

[56] References Cited

U.S. PATENT DOCUMENTS

| | | | |
|---|---|---|---|
| Re. 32,518 | 10/1987 | Miyasaka et al. | 546/48 |
| 3,219,529 | 11/1965 | Nash et al. | |
| 3,699,230 | 10/1972 | Beauchamp, Jr. et al. | |
| 3,894,029 | 7/1975 | Winterfeldt et al. | |
| 4,031,098 | 6/1977 | Sugasawa et al. | |
| 4,082,881 | 4/1978 | Chen et al. | |
| 4,228,162 | 10/1980 | Luzzi et al. | |
| 4,339,276 | 7/1982 | Miyasaka et al. | 491/22 |
| 4,342,776 | 8/1982 | Cragoe, Jr. et al. | 424/274 |
| 4,399,282 | 8/1983 | Miyasaka et al. | 491/147 |
| 4,473,692 | 9/1984 | Miyasaka et al. | 546/48 |
| 4,513,138 | 4/1985 | Miyasaka et al. | 546/48 |
| 4,545,880 | 10/1985 | Miyasaka et al. | 204/158 |
| 4,604,463 | 8/1986 | Miyasaka et al. | 544/125 |
| 4,734,284 | 3/1988 | Terada et al. | |
| 4,774,236 | 9/1988 | Cook et al. | 514/176 |
| 4,775,759 | 10/1988 | Rice et al. | 546/44 |
| 4,778,891 | 10/1988 | Tagawa et al. | 546/18 |
| 4,820,816 | 4/1989 | Evans et al. | 540/205 |
| 4,894,456 | 1/1990 | Wall et al. | 546/41 |
| 4,914,205 | 4/1990 | Sawada et al. | 546/70 |
| 4,981,968 | 1/1991 | Wall et al. | 544/361 |
| 5,004,758 | 4/1991 | Boehm et al. | 514/283 |
| 5,049,668 | 9/1991 | Wall et al. | 540/481 |
| 5,053,512 | 10/1991 | Wani et al. | 546/41 |
| 5,061,800 | 10/1991 | Wall et al. | 514/219 |
| 5,106,742 | 4/1992 | Wall et al. | 435/233 |
| 5,180,722 | 1/1993 | Kalsha | 546/48 |
| 5,225,404 | 7/1993 | Giovannella et al. | 514/81 |
| 5,447,936 | 9/1995 | Hausheer et al. | 514/283 |
| 5,496,830 | 3/1996 | Shapiro et al. | 514/283 |

FOREIGN PATENT DOCUMENTS

| | | |
|---|---|---|
| 2087209 | 1/1993 | Canada . |
| 0074256 | 3/1983 | European Pat. Off. . |
| 0074770 | 3/1983 | European Pat. Off. . |
| 0088642 | 9/1983 | European Pat. Off. . |
| 0220601 | 5/1987 | European Pat. Off. . |
| 0325247 | 7/1989 | European Pat. Off. . |
| 58-154583 | 9/1983 | Japan . |
| 58-154584 | 9/1983 | Japan . |
| 59-5188 | 1/1984 | Japan . |
| 59-51287 | 3/1984 | Japan . |
| 59-51289 | 3/1984 | Japan . |
| 59-227884 | 12/1984 | Japan . |
| 61-50985 | 3/1986 | Japan . |
| 61-85389 | 4/1986 | Japan . |
| 62-195384 | 8/1987 | Japan . |

OTHER PUBLICATIONS

Seigo Sawada, et al., Chemical modification of an antitumor alkaloid camptothecin: Synthesis and antitumor activity of 7–C–substituted camptothecins. Chemical and Pharmaceutical Bulletin, 39(10):2574–2580, 1991.

M.E. Wall, et al., Plant antitumor agents. 22. Isolation of 11–hydroxycamptothecin from Camptotheca acuminata Decne: Total synthesis and biological activity. Journal of Medicinal Chemistry, 29(8):1553–1555, 1986.

Potmesil, Milan, et al., Camptothecins: From Bench Research to Hospital Words. Cancer Research 54:1431–1439, Mar. 1994.

Oncology Bulletin, pp. 4–5, Apr. 1994.

*Primary Examiner*—Donald G. Daus
*Attorney, Agent, or Firm*—Thomas J. Dodd

[57] ABSTRACT

The novel compounds 11-hydroxy-7-ethyl camptothecin and 11-hydroxy-7-methoxy camptothecin (11,7-HECPT and 11,7-HMCPT) are active anticancer compounds which are poorly soluble in water. Because of their novelty, 11,7-HECPT and 11,7-HMCPT derivatives have not been directly administered by parenteral or oral routes to human subjects as an antitumor composition for the purpose of inhibiting the growth of cancer cells. The claimed compositions are useful as compared to the water soluble camptothecin derivatives, such as CPT-11, in clinical trials. The unpredictable interpatient variability in the metabolic production of an active metabolite from CPT-11 limits the utility of CPT-11. This invention overcomes these limitations by claiming novel pharmaceutically acceptable lactone stable formulations of 11,7-HECPT or 11,7-HMCPT, to directly administer to patients. The present invention also claims 11,7-HECPT and 11,7-HMCPT compositions, the synthesis of 11,7-HECPT or 11,7-HMCPT, the methods of formulation of 11,7-HECPT or 11,7-HMCPT, and the methods of use of 11,7-HECPT or 11,7-HMCPT. Additionally, the claimed invention is directed to novel dosages, schedules, and routes of administration for both the 11,7-HECPT or 11,7-HMCPT formulations to humans with various forms of cancer. Other embodiments of this invention include isolation methods and methods of synthesis of certain camptothecin derivatives.

42 Claims, No Drawings

11,7 SUBSTITUTED CAMPTOTHECIN DERIVATIVES AND FORMULATIONS OF 11, 7 SUBSTITUTED CAMPTOTHECIN DERIVATIVES AND METHODS FOR USES THEREOF

This is a divisional of application Ser. No. 08/229,527, filed Apr. 19, 1994 now U.S. Pat. No. 5,468,754.

BACKGROUND OF THE INVENTION

1. Field of the Invention

Three related compounds, 11-hydroxy-7-methoxy-camptothecin (11,7-HMCPT), 11-hydroxy camptothecin (11-HCPT) and 11-hydroxy 7-ethyl camptothecin (11,7-HECPT), which have previously demonstrated antitumor activity, have not yet been further developed due to poor water solubility. Additionally, these compounds have not been further developed because of structural modifications due to synthetic inefficiency in the preparation of 11,7 substituted camptothecins using shorter synthetic schemes than total synthesis. This invention overcomes these limitations and claims novel compositions of matter, pharmaceutically acceptable formulations of 11,7-HECPT and 11,7-HMCPT and antitumor compositions comprising 11,7-HECPT and 11,7-HMCPT. Additionally, this invention claims novel dosages, schedules of administration, and routes of administration for both 11,7-HECPT and 11,7-HMCPT formulations to humans with various forms of cancer.

2. Description of the Related Art

A. Introduction

Camptothecin (CPT) is highly water insoluble. The creation of water soluble derivatives of camptothecin has been the subject of pursuit by many investigators in order to simplify or eliminate several significant technical problems associated with administration of this class of highly water insoluble drugs.

One water soluble derivative of camptothecin is CPT-11. CPT-11 has undergone Phase I and Phase II clinical trials in human patients with cancer. CPT-11 is a product which requires metabolic conversion to an active species. Metabolic conversion of CPT-11 (a water soluble derivative of camptothecin) to its active metabolite, 10-hydroxy-7-ethyl camptothecin (SN38), varies from patient to patient. This required conversion of CPT-11 to SN38 limits the utility of CPT-11 because of the difficulty in reliably and safely achieving the highest tolerated plasma concentrations of SN38 in the patient.

SN38 is poorly soluble in water. The conversion of CPT-11 to SN38 involves a putative carboxyl esterase enzyme, which is believed to be mainly responsible for the metabolic production of SN38 from CPT-11. Human lung cancer cell lines have been observed to convert less CPT-11 to SN38 than normal cells. The cancer cells' decreased metabolic conversion represents a form of resistance to CPT-11 and limits the utility of CPT-11 in terms of reliably and safely achieving adequate plasma concentrations of SN38 to inhibit the growth of cancer cells in humans. 11-hydroxy-7-alkoxy camptothecins, 11-hydroxy-7-alkyl camptothecin represent another new class of antitumor compounds. These compounds do not require metabolic activation to produce active species, and like camptothecin are highly water insoluble.

The present invention, using both 11,7-HECPT and 11,7-HMCPT, takes advantage of the high lipid solubility and the lack of metabolic activation along with formulation art which permits direct administration of these camptothecin derivatives to human patients with cancer.

Until now, 11,7-HECPT and 11,7-HMCPT derivatives of camptothecin have not been described because of prior art which teaches that water insolubility generally renders alkyl substituted camptothecins unsuitable for direct clinical use because of limitations in pharmaceutical formulations.

This invention teaches the formulation of two specific camptothecin (CPT) derivatives, namely 11-hydroxy-7-methoxy camptothecin (11,7-HMCPT) and 11-hydroxy-7-ethyl camptothecin (11,7-HECPT) in a pharmaceutically acceptable manner using an organic solvent or a mixture of organic cosolvents which permit direct administration of these species of CPT to cancer patients.

This invention also provides certain indications, schedules, dosages and routes of administration for 11,7-HECPT and 11,7-HMCPT for the purpose of treating cancer in humans. The selection of suitable organic solvents for pharmaceutical dosage formulations of the claimed invention is limited to organic solvents with a high degree of physiological safety.

Additionally, this invention teaches administration of 11,7-HECPT or 11,7-HMCPT in a pharmaceutically acceptable multi-solvent formulation. The claimed formulations overcome interpatient variability and biochemical drug resistance which are associated with the use of CPT-11.

The claimed invention also teaches the use of 11,7-HECPT and 11,7-HMCPT in treating human patients with cancer where the cancer cells may have become resistant to metabolic conversion of CPT-11 to SN38 because of altered enzymatic activity.

B. DNA Topoisomerases

Several clinically important anticancer drugs kill tumor cells by affecting DNA topoisomerases. Topoisomerases are essential nuclear enzymes that function in DNA replication and tertiary structural modifications, such as overwinding, underwinding, and catenation, which normally arise during replication, transcription, and perhaps other DNA processes. The two major topoisomerases that are ubiquitous to all eukaryotic cells are topoisomerase I (topo I), which cleaves single stranded DNA, and topoisomerase II (topo II), which cleaves double stranded DNA. Topoisomerase 1 is involved in DNA replication; it relieves the torsional strain introduced ahead of the moving replication fork.

Topoisomerase I, purified from human colon carcinoma cells or calf thymus, is inhibited by camptothecin, a water soluble analog (CPT-11), and its proposed active metabolite, 10-hydroxy-7-ethyl camptothecin (also known as SN38). Another water soluble Topo I inhibitor in clinical trials is topotecan. These camptothecin derivatives inhibit the enzyme by an identical mechanism; they stabilize the covalent complex of enzyme and strand-cleaved DNA, which is an intermediate in the catalytic mechanism. The compounds have no binding affinity for either isolated DNA or topoisomerase I but bind with measurable affinity to the enzyme-DNA complex. The stabilization of the topoisomerase I"cleavable complex" by camptothecins with intact lactone E-ring is readily reversible. Although camptothecins generally have no effect on topoisomerase II, camptothecin, CPT-11 and SN38 stabilize the "cleavable complex" in a manner analogous to the way in which epipodophyllotoxin glycosides and various anthracyclines inhibit topoisomerase II.

Inhibition of topoisomerase I by camptothecin induces protein-associated-DNA single strand breaks. Virtually all of the DNA strand breaks observed in cells treated with certain camptothecin derivatives are protein linked, whereas an increase in unexplained protein-free breaks can be detected in L1210 cells treated with camptothecin. The compounds appear to produce identical DNA cleavage patterns in end-labeled linear DNA. Under no circumstance has it been demonstrated that camptothecin, CPT-11, SN38, or topotecan cleaves DNA in the absence of the topoisomerase I enzyme.

C. Activity of Camptothecin, HECPT, HMCPT, Topotecan and CPT-11 is Cell Cycle Specific The antitumor activity of camptothecins is cell cycle specific. The greatest quantitative biochemical effect observed in cells exposed to camptothecin is DNA single strand breaks that occur during the S-phase. Because the S-phase is a relatively short phase of the cell cycle, longer exposure to the drugs results in increased cell killing. Brief exposure of tumor cells to the drugs produces little or no cell killing, and quiescent cells are refractory. These results are likely due to two factors:

(1) The drugs inhibit topoisomerase I reversibly. Although they may produce potentially lethal modifications of the DNA structure during DNA replication, the breaks may be repaired after washout of the drug; and (2) Cells treated with topo I inhibitors such as camptothecin tend to stay in $G^o$ of the cell cycle until the drug is removed and the cleaved DNA is repaired. Inhibitors of these enzymes can affect many aspects of cell metabolism including replication, transcription, recombination, and chromosomal segregation.

D. Lactone Form Stabilizes Antitumor Activity of Camptothecin and its Derivatives with the Native E Ring.

Researchers have demonstrated by HPLC, NMR and other techniques that camptothecin, topotecan, CPT-11, and other camptothecin derivatives undergo an alkaline, pH-dependent hydrolysis of the E-ring lactone. The slow reaction kinetics allow one to assess whether both the lactone and non-lactone forms of the drug stabilize the topoisomerase I-cleaved DNA complex. Studies indicate that only the closed lactone form of camptothecin helps stabilize the cleavable complex. This observation provides some rationale for the high degree of activity observed in solid tumor models with exposure to camptothecin. Tumor cells, particularly hypoxic cells prevalent in solid neoplasms, have lower intracellular pH levels than normal cells. At pH levels below 7.0, the lactone form of camptothecin predominates. Thus, one would predict that the drug will be more effective at inhibiting topoisomerase I in acidic cells than in cells having higher intracellular pH levels.

Camptothecin, CPT-11 and Topotecan

Wall and Wani isolated camptothecin from the plant, *Camptotheca acuminata*, in 1966. In the early 1970's, camptothecin reached Phase I trials and was found to have some antitumor activity, but it caused unpredictable myelosuppression and hemorrhagic cystitis. Phase 11 studies with sodium camptothecin were limited because they induced unpredictable and severe myelosuppression, gastrointestinal toxicity, hemorrhagic cystitis, and alopecia. Clinical trials with sodium camptothecin were eventually discontinued because of these unpredictable toxicities and the lack of significant anti-tumor activity.

Two camptothecin derivatives, CPT-11 and topotecan, have less sporadic toxicities but retain the significant antitumor activity of the parent compound. CPT-11 and topotecan are undergoing Phase I and Phase II development in the United States. 10,11-methylene dioxycamptothecin (MDCPT)is reportedly very active in preclinical studies, but it is also reported to be relatively insoluble in water which reportedly limits its use in the clinic.

Tables 1 and 2 present data summarizing Phase I and Phase II clinical trials of CPT-11. Neutropenia and diarrhea are the major reported, dose-limiting toxicities of CPT-11.

TABLE 1

PHASE I STUDIES OF CPT-11

| investigator | Schedule | # Pts | Dose | Toxicity | Tumor Type |
| --- | --- | --- | --- | --- | --- |
| Clavel et al | 90 min. QD × 3 Q21 days | 37 | 115 mg/m2/d (33–115) | Neutropenia* diarrhea, nausea and vomiting, alopecia | Breast (1 PR) Mesothelioma (1 PR) |
| Culine et al | 90 min. Q21 days | 59 | 150 mg/m2/wk (50–150) | Neutropenia* diarrhea* vomiting, alopecia fatigue stomatitis Neutropenia* | esophagus (1PR) cervix (1PR) renal (1PR) ovarian (1PR) |
| Negoro et al | 30 min infusion weekly | 17 | 100 mg/m2 (50–150) | Diarrhea*, N/V, alopecia, liver dysfunction | NS CLC (2PRs) |
| Ohe et al | 120 hr Cl Q3 wks | 36 | 40 mg/m2/d (5–40) | Diarrhea* nausea and vomiting, thromobocytopenia, anemia, liver dysfunction Diarrhea* | None |
| Rothenberg et al | 90 mg QW × 4 Q42 days | 32 | 180 mg/m2/wk (50–180) | Neutropenia, nausea, vomiting, alopecia | Colon Ca (2 PRs) |

TABLE 1-continued

PHASE I STUDIES OF CPT-11

| investigator | Schedule | # Pts | Dose | Toxicity | Tumor Type |
|---|---|---|---|---|---|
| Rowinsky et al | 90 min infusion Q21 day | 32 | 240 mg/m2 (100–345) | Neutropenia* vomiting, diarrhea abd. pain, flushing | Colon Ca (1PR) Cervix Ca (1 PR) |

*Dose Limiting Toxicity
__Dated updated, unpublished

TABLE 2

CPT-11 PHASE II TRIALS

| INVESTIGATOR | TUMOR TYPE | SCHEDULE | # Pts. | RESPONSE | |
|---|---|---|---|---|---|
| Fukuoka et al | Untreated Non Small Cell Lung Cancer | 100 mg/m$^2$ weekday | 73 | (23/72) PRs 31.9% | Neutropenia diarrhea, nausea, vomiting, anorexia, alopecia |
| Masudu et al | Refractory or Relapsed Small Cell Lung Cancer | 100 mg/m$^2$ weekly | 16 | (7/15) PRs 47% | Neutropenia, diarrhea, Neutropenia, diarrhea, (12.5%) |
| Negoro et al | Small Cell Lung Cancer | 100 mg/m$^2$/week | 41 | 2 CRs and 7 PRs 33.3% | Neutropenia (38.6%) N/V (61.5%) diarrhea (53.8%) alopecia (40.0%) |
| Ohono et al | Leukemia/ Lymphoma | 200 mg Q3 No resp. 34% PR 40 mg/m$^2$ Q0 × 5 20 mg/m$^2$ bid × 7 25% RR | 62 | ** | Neutropenia (91%) Thromocytopenia Gastrointestinal (76%) |
| Shimada et al | Colon cancer | 100 mg/m$^2$/week or 150 mg/m$^2$/Q 2 wks | 17 | 6/17(PR) 46% | Neutropenia (53%) N/V (35%) diarrhea (24%) |
| Takeuchi et al | Cervical cancer | 100 mg/m$^2$ weekly 150 mg/m$^2$ weeks | 69 | SCR 8PR RR of 23.6% | Neutropenia (89%) N/V (51%) Diarrhea (39.1%) Alopecia (38.1%) |

F. Water Insoluble SN38 is the Active Metabolite of CPT-11

Preclinical data obtained from animals and more recent data obtained from humans by Barilero et al. suggest that SN38 is the active metabolite of CPT-11 in vivo. Several different researchers administered CPT-11 intravenously during Phase I trials and recorded the peak plasma concentrations (CpMax) at the end of the infusions. An analysis of the published mean peak plasma concentrations indicates that approximately 1.5% to 9% of the administered CPT-11 (on a per/mg basis) is converted into SN38. The pharmacokinetic data from 30-minute intravenous infusions show a lower percentage of conversion (approximately 1.5%) of CPT-11 to SN38 than that observed following more prolonged infusions (approximately 9% at 40 mg/m$^2$/d×5). The reported half life of SN38 observed in humans following the administration of CPT-11 ranges from 8.8 to 39.0 hours.

The biochemical and pharmacologic relationship between CPT-11 and SN38 and the role of theses compounds in killing cancer cells in vivo is not completely understood. Investigators looking at tumor cell lines in vitro have reported that SN38 has 3600-fold greater inhibitory activity than CPT-11 against topoisomerase I enzyme of P388 cells and that SN38 is approximately 1000-fold more potent in generating single-strand DNA breaks in MOLT3 cells. However, Kaneda et al. report that SN38 has little anti-tumor activity compared to CPT-11 in vivo. They base their findings on studies conducted using an intermittent bolus schedule (days 1, 5, and 9) and an intraperitoneal route of administration with an intraperitoneal P388 tumor model in mice. The inventors believe that the activity of SN38 would have been observed to be greater had these investigators increased the duration of drug exposure instead of using an intermittent bolus schedule.

Ohe et al. suggest that SN38 is a more toxic moiety of CPT-11 and could be responsible for much of the toxicity attributed to CPT-11. However, these same investigators noted a lack of correlation between SN38 pharmacokinetics and dose or CPT-11 pharmacokinetics and toxicity in human subjects. Furthermore, Ohe et al. noted a large range of interpatient variability in the AUC of CPT-11 and its metabolism to SN38, which may result in unpredictable variability in the pharmacokinetic behavior, clinical antitumor effects, and toxicity in the individual patient. The data Ohe et al. obtained (using a 5-day, continuous intravenous infusion of CPT-11) also suggests that the conversion of CPT-11 to SN38 is a saturable process. If this is so, the clinical approach to maximizing dose intensity of the SN38 active metabolite would impose additional limitations on the effective use of CPT-11 in patients with cancer.

In preclinical studies of xenografts of human tumors in nude mice, Kawato et al. report that the sensitivity of human tumors to CPT-11 is independent of their ability to produce SN38 and that the effectiveness of CPT-11 is not related to the ability of the tumor to produce SN38. The Kawato et al. report suggests further that SN38 production is likely to be mediated in the plasma or interstitial compartment. Kaneda et al. observed that the plasma concentration of SN38 in mice was maintained longer after CPT-11 administration than after treatment with SN38 and suggested that clinicians should maintain plasma levels of SN38 to enhance the antitumor activity of CPT-11. One of the advantages of present invention provides clinicians with the ability to directly adjust the plasma levels of 11,7-HECPT or 11,7-HMCPT derivatives to the point of therapeutic tolerance by controlling the dose and schedule of administration, which should lead to a superior ability to achieve better anti-tumor activity and reduce the interpatient variability of the plasma levels of 11,7-HECPT or 11,7-HMCPT.

The different types of observations made in these studies suggest that direct administration of 11,7-HECPT or 11,7-HMCPT by parenteral and oral administration could provide significant clinical benefit for patients with cancer which is amenable to treatment with this type of agent. However, in the past, similar hydrophobic camptothecin derivatives have been considered insufficiently water soluble for clinical use. The current invention overcomes this problem by providing lactone stable pharmaceutically acceptable multisolvent formulations of 11,7-HECPT for parenteral use and also oral 11,7-HECPT formulations.

This invention teaches novel 11-hydroxy modified camptothecins with 7-alkyl or 7-alkoxy modifications as new compositions of matter. These novel compounds which contain the 11-hydroxy or 11-alkoxy modifications of 7-alkyl or 7-alkoxy camptothecins represent new camptothecin derivatives, which are useful for the treatment of human cancers. Like many of the camptothecins, these molecules are generally poorly soluble in water and are more lipid soluble. Greater lipid solubility will facilitate diffusion of these molecules and permit more effective tissue penetration than the water soluble camptothecin species, such as CPT-11, E-ring opened carboxylate forms of camptothecin, or cationic species of camptothecins. To the inventor's knowledge, neither 11-hydroxy-7-ethyl camptothecin (11,7-HECPT), 11-hydroxy-7-methoxy camptothecin (11,7-HMCPT) or 11-hydroxy-7-alkoxy camptothecin have been directly administered to human subjects for the purpose of inhibiting the growth of cancer cells. This invention overcomes the above mentioned limitations and claims novel pharmaceutically acceptable formulations of 11,7-HECPT, and 11,7-HMCPT, methods of administration of 11,7-HECPT and 11,7-HMCPT, and antitumor compositions comprising solutions of 11,7-HECPT and solutions of HMCPT. Additionally, this invention claims novel dosages, schedules of administration, and routes of administration for both 11,7-HECPT and 11,7-HMCPT formulations to humans with various forms of cancer.

SUMMARY OF THE INVENTION

In general, this invention claims composition of matter directed to camptothecin derivatives containing certain modifications at the 11 and 7-positions of camptothecin (CPT) and 11-hydroxy-7-alkoxy camptothecin. This invention also claims methods for chemical synthesis of these compounds, the methods of formulation of these compounds, and methods of use of 11-hydroxy-7-ethyl camptothecin (11,7-HECPT), 11-hydroxy, 7-methoxy CPT (HMCPT) and 11-hydroxy-7-alkoxy camptothecin to treat cancer in human subjects. In the case of intravenous administration of 11,7-HECPT or 11,7-HMCPT, several schedules and dosages produce sufficient levels of 11,7-HECPT or 11,7-HMCPT to yield beneficial antitumor effects in humans. The effective levels of 11,7-HECPT or 11,7-HMCPT are safe in terms of the incidence and severity of certain side effects that may occur with administration and are acceptable within standard medical practice for patients undergoing treatment for cancer.

This invention contains the following novel chemical composition, methods of synthesis, methods of formulation, and methods of use components.

In general, this invention teaches the formulation of two specific types of camptothecin derivatives, namely 11-hydroxy-7-methoxy camptothecin (11,7-HMCPT) and 11-hydroxy, 7-ethyl camptothecin (11,7-HECPT)in a pharmaceutically acceptable manner using an organic solvent or a mixture of organic cosolvents which permit direct administration of these species of CPT to cancer patients.

This invention also provides certain indications, schedules, dosages and routes of administration for 11,7-HECPT and 11,7-HMCPT for the purpose of treating cancer in humans. The selection of suitable organic solvents for pharmaceutical dosage formulations of the claimed invention is limited to organic solvents with a high degree of physiological safety.

Additionally, this invention teaches administration of 11,7-HECPT or 11,7-HMCPT in a pharmaceutically acceptable multi-solvent formulation. The claimed formulations overcome interpatient variability and biochemical drug resistance which are associated with the use of CPT-11.

The claimed invention also teaches the use of 11,7-HECPT and 11,7-HMCPT in treating human patients with cancer where the cancer cells may have become resistant to metabolic conversion of CPT-11 to SN38 because of altered enzymatic activity.

One embodiment of the claimed invention are the compounds 11-hydroxy 7-ethyl camptothecin, 11-hydroxy 7-methoxy camptothecin and 11- hydroxy camptothecins with or without 7-alkyl or 7-alkoxy modifications.

Another embodiment of the claimed invention is a 7, 11-substituted camptothecin derivative having the formula:

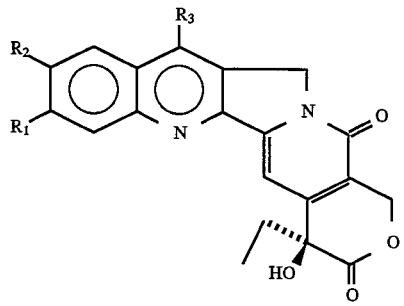

wherein R1 represents an alkoxy group, an alkoxyaryloxy group, a hydroxyl group, an acyloxy group, or an aryloxy group; wherein R2 represents a hydrogen; and wherein R3 represents a lower alkyl group, a substituted alkyl aromatic group, a benzyl group,an alkylhydroxyl group, an alkylaroxyl group, or an acyloxy derivative.

Yet another embodiment of the claimed invention is an 11-Hydroxy-7-Methoxy Camptothecin having the formula:

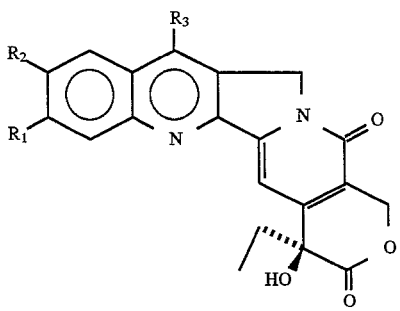

wherein R1 represents —OH; wherein R2 represents —H; and wherein R3 represents methoxy.

For the purpose of the claimed invention, the following definitions and lists are provided.

Sub crop:

Repeated recovery of a desired product via pooling of an impure mixture obtained from the first batch of fractional separation.

Mother liquor:

The main solvent portion and subsequent washings that contain the desired product. The mother liquor becomes contaminated with impurities during recrystallization step.

Soxhlet Extractor:

A glass apparatus used for the effective separation of a material that has preferential solubility in a particular solvent as compared to the rest of the components in a mixture.

Volatile carboxylic acid:

This acid is a low boiling organic acid. Examples of a volatile carboxylic acid are formic acid, acetic acid, trifluoroacetic acid, and propionic acid.

Quartenization:

This process describes how weak organic bases, such as tertiary nitrogen atoms, can be converted to corresponding salts ionic in nature by treating a weak organic base with either a carboxylic acid or a mineral acid.

Examples of chromatography:

Examples of chromatography include: Silica gel chromatography, cellulose chromatography, ion-exchange chromatography, reverse phase chromatography, gel filtration chromatography, and florisil chromatography. For the purpose of this invention, the inventors prefer to use silica gel chromatography.

Lower case alcohols:

Lower case alcohols are alcohols that boil below 125° C. Examples of lower cases alcohols are methanol, ethanol, propanol, isopropanol, butanol, 2-butanol, isobutanol, and tertiary butanol.

Method to Purify Individual CPT Mono-Substituted Derivatives from a Mixture of Isomer CPTs As a preferred embodiment of the claimed invention, an efficient, inexpensive, and scalable chromatographic technology is developed to obtain 10-hydroxycamptothecin and 11-hydroxy camptothecin in +95% purity from a readily available natural mixture of 10 & 11-hydroxycamptothecin (2:1). This novel separation methodology also permits isolation of certain key positional isomers of camptothecins.

Yet another embodiment of this invention is to develop a new single step large scale conversion of unprotected 11-phenolic camptothecin to 7-alkyl-11-phenolic camptothecin and other A ring substituted phenolic camptothecin series.

More specifically, an embodiment of the claimed invention is a purification method for isolating individual camptothecin mono-substituted 10, 11 derivatives from a mixture of various position isomers of CPT comprising the following steps: a) dissolve naturally occurring mixture of 10-hydroxy CPT and 11-hydroxy CPT with a suitable quartenizing reagent to produce a homogeneous solution; b) separate the 10-substituted CPT from the 11-substituted CPT using chromatography; c) recover faster migrating 11-substituted CPT isomer from chromatogram step (b); and (d) elute and recover slower migrating 10-substituted CPT isomer from chromatogram step (b) using a step wise gradient.

Additionally, this purification method is further defined wherein the quartenizing reagent is selected from the group consisting of trifluoroacetic acid, methanolic hydrochloric acid, aqueous hydrochloric acid, and any volatile carboxylic acid and wherein the chromatography method is selected from the group consisting of silica gel chromatography, cellulose chromatography, ion-exchange chromatography, reverse phase chromatography, gel filtration chromatography, and florisil chromatography. This purification method is further defined wherein the step wise gradient in step (d) is further defined as methanol:chloroform:triethylamine in the ratio of 1:1:0.1.

Yet another embodiment of the claimed invention is a purification method for isolating individual disubstituted 7,10 or 7,11 camptothecin derivatives comprising the following steps: a) dissolve naturally occurring mixture of 10-hydroxy CPT and 11-hydroxy CPT with a quartenizing reagent to produce a homogeneous solution; b) separate the 10-substituted CPT from the 11-substituted CPT using chromatography; c) recover faster migrating 11-substituted CPT isomer from chromatogram step (b); and d) elute and recover slower migrating 10-substituted CPT isomer from chromatogram step (b) using a step wise gradient.

This purification method is further defined wherein the quartenizing reagent is selected from the group consisting of wherein the trifluoroacetic acid, methanolic hydrochloric acid, aqueous hydrochloric acid, and any volatile carboxylic acid and wherein the chromatography is a silica gel column chromatography. This purification method is further defined wherein the step wise gradient is methanol:chloroform:triethylamine in a ratio of 1:1:0.1.

Another embodiment of the claimed invention is a purification method for isolating 10-Hydroxy Camptothecin comprising the following steps: a) charge a mixture of isomeric camptothecin into a suitable cellulose thimble of a Soxhlet apparatus; b) charge a suitable lower case alcohol into the Soxhlet apparatus; c) continuously extract out 10-HCPT from refluxing solvent; d) intermittently withdraw collected solvent from the receiver and charge fresh batch with lower case alcohol until extraction is completed; and e) recrystallize residue to obtain 10-HCPT. Additionally, this purification process is further defined wherein the suitable lower case alcohol is ethyl alcohol.

Yet another embodiment of the claimed invention is a purification method for isolating 11-Hydroxy Camptothecin comprising the following steps: a) charge a mixture of isomeric camptothecin into a suitable cellulose thimble of a Soxhlet apparatus; b) charge a suitable lower case alcohol into the Soxhlet apparatus; c) intermittently withdraw collected solvent from the receiver and charge fresh batch with lower case alcohol until extraction is completed; and d) recrystallize residue inside the thimble to obtain 11-HCPT. This purification is further defined wherein the suitable lower case alcohol is ethyl alcohol.

Yet another embodiment of the claimed invention is a purification method for isolating 10-Hydroxy polysubstituted Camptothecin comprising the following steps: a) charge a mixture of polydisubstituted camptothecin into a cellulose thimble of a Soxhlet apparatus; b) charge a suitable lower case alcohol into the Soxhlet apparatus; c) continuously extract out 10-Hydroxy polysubstituted Camptothecin derivative from refluxing solvent; d) intermittently withdraw collected solvent from the receiver and charge fresh batch with lower case alcohol until extraction is completed; and e) recrystallize residue to obtain 10-Hydroxy polysubstituted. A further embodiment of the claimed purification process is where the suitable lower case alcohol is ethyl alcohol.

Another embodiment of the invention is to successfully extend the application of this newly developed chromatographic methodology to separate mixtures of 7-alkyl-10-hydroxy and 7-alkyl-11-hydroxy camptothecins (2:1) and mixtures of 10 & 11-O-protected camptothecins (1:1) in +95% purity.

Yet another embodiment of this invention is a high yield single step large scale chemical transformation of 10-hydroxy camptothecin to 7-alkyl-10-hydroxy camptothecin. To the inventor's knowledge, this is the first time such chemical transformations are reported on unprotected phenolic camptothecins.

More specifically, this invention further embodies a process for preparing a 7, 10-disubstituted Camptothecin derivative having the formula:

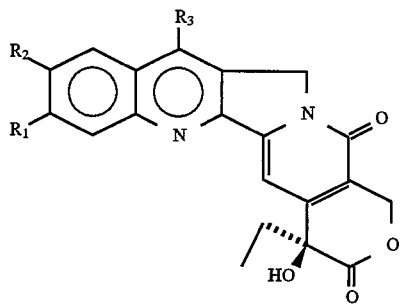

wherein R1 represents a hydrogen; wherein R2 represents an hydroxy group, an acyloxy group, an alkoxy group, or an aryloxy group; wherein R3 represents a lower alkyl group, an alkylhydroxyl group, an alkylaroxyl group, an acyloxy derivative, a benzyl group, or a substituted alkylaromatic group; and wherein the process comprises the following steps: a) suspend 10-hydroxy camptothecin in water; b) add ferrous salt and stir well; c) add an aldehyde, a carboxylic acid or an alcohol; d) add concentrated sulfuric acid; e) add 30% hydrogen peroxide dropwise; f) stir the reaction mixture allowing the temperature to slowly rise to room temperature; and g) isolate the desired product from the reaction mixture in step (f). Yet another embodiment of the claimed invention is a process wherein the ferrous salt is further defined as iron sulfate heptahydrate and the aldehyde is further defined as propionaldehyde.

An additional embodiment of the claimed invention is a process for preparing 10-Hydroxy-7-Ethyl Camptothecin having the formula:

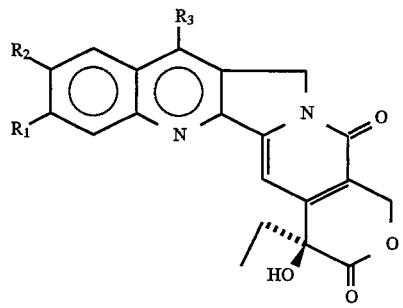

wherein R1 represents a hydrogen; wherein R2 represents hydroxy; wherein R3 represents ethyl; and wherein the process comprises the following steps: a) suspend 10-hydroxy camptothecin in water; b) add ferrous salt and stir well; c) add an aldehyde, a carboxylic acid or an alcohol; d) add concentrated sulfuric acid; add 30% hydrogen peroxide dropwise; f) stir the reaction mixture allowing the temperature to slowly rise to room temperature; and g) isolate the desired product from the reaction mixture in step (f). A further embodiment of this process is wherein the aldehyde is further defined as propionaldehyde and the ferrous salt is further defined as iron sulfate heptahydrate.

Yet another embodiment of the claimed invention is a process for preparing a 7,11-disubstituted Camptothecin derivative having the formula:

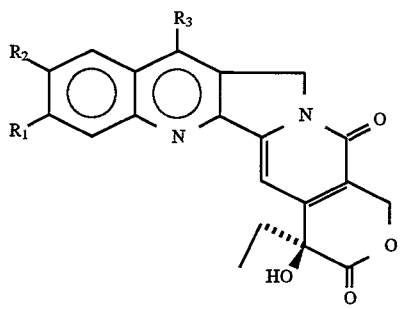

wherein R1 represents hydroxy; wherein R2 represents hydrogen; wherein R3 represents a lower alkyl group, an alkylhydroxyl group, an alkylaroxyl group, an aroxyalkyl group, an acyloxy derivative, or a substituted alkylaromatic group; and wherein the process comprises the following steps: a) suspend 11-Hydroxy Camptothecin in water; b) add ferrous salt and stir well; c) add an aldehyde, a carboxylic acid or an alcohol; d) add concentrated sulfuric acid; e) add 30% hydrogen peroxide dropwise; f) stir the reaction mixture allowing the temperature to slowly rise to room temperature; and g) isolate the desired product from the reaction mixture in step (f). The claimed invention is further defined wherein the aldehyde is propionaldehyde and the ferrous salt is iron sulfate heptahydrate.

Yet another embodiment of the claimed invention is a process for preparing 11-Hydroxy-7-Ethyl Camptothecin having the formula:

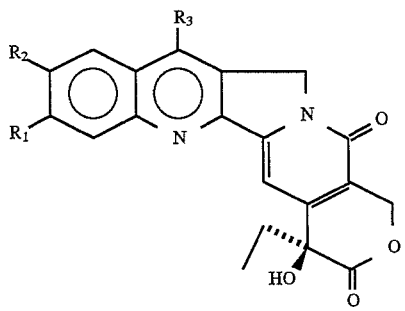
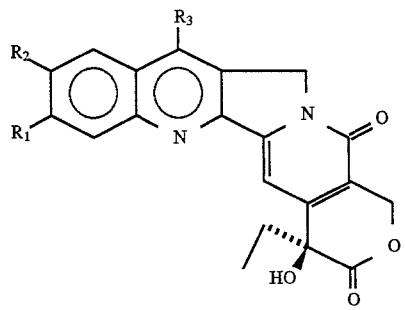

wherein R1 represents hydroxyl wherein R2 represents hydrogen; wherein R3 represents ethyl; and wherein the process comprises the following steps: a) suspend 11-Hydroxy Camptothecin in water; b) add ferrous salt and stir well; c) add an aldehyde, a carboxylic acid or an alcohol; d) add concentrated sulfuric add; e) add 30% hydrogen peroxide dropwise; f) stir the reaction mixture allowing the temperature to slowly rise to room temperature; and g) isolate the desired product from the reaction mixture in step (f). This invention is further defined wherein the aldehyde is propionaldehyde and the ferrous salt is iron sulfate heptahydrate.

Another embodiment of the claimed invention is a process for preparing a 7, 10-disubstituted Camptothecin derivative having the formula:

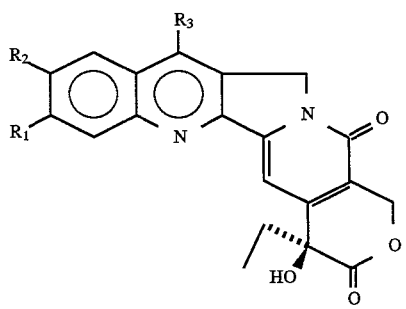

wherein R1 represents a hydrogen; wherein R2 represents an hydroxy group, an acyloxy group, an alkoxy group, or an aryloxy group; wherein R3 represents a lower alkyl group, an alkylhydroxyl group, an alkylaroxyl group, an acyloxy derivative, or a substituted alkyl aromatic group; and wherein the process comprises the following steps: a) suspend 10-Hydroxy Camptothecin in water; b) add ferrous salt and stir well; c) add an aldehyde, a carboxylic acid or an alcohol; d) add a volatile carboxylic acid at low temperature; e) add a suitable free radical generator; and f)isolate 7,10 disubstituted Camptothecin using a suitable chromatography method. This claimed invention is further defined wherein the aldehyde is propionaldehyde, the ferrous salt is iron sulfate heptahydrate, and the volatile carboxylic acid is trifluoroacetic acid. This claimed process is further defined wherein the suitable free radical generator is selected from the group consisting of potassium persulfate and ammonium persulfate and the chromatography method is selected from the group consisting of silica gel chromatography, cellulose chromatography, ion-exchange chromatography, reverse phase chromatography, gel filtration chromatography, and florisil chromatography.

Another embodiment of the claimed invention is a process for preparing 10-Hydroxy-7-Ethyl Camptothecin having the formula:

wherein R1 represents a hydrogen; wherein R2 represents hydroxyl; wherein R3 represents ethyl; and wherein the process comprises the following steps: a) suspend 10-Hydroxy Camptothecin in water; b) add ferrous salt and stir well; c) add an aldehyde, a carboxylic acid or an alcohol; d) add a volatile carboxylic acid at low temperature; e) add a suitable free radical generator; and f)isolate 10-Hydroxy-7-Ethyl Camptothecin using a suitable chromatography method.

The process of the claimed invention is further defined wherein the aldehyde is propionaldehyde, the ferrous salt is iron sulfate heptahydrate, the volatile carboxylic acid is trifluoroacetic acid, and the suitable free radical generator is selected from the group consisting of potassium persulfate and ammonium persulfate. This claimed process is further defined wherein the chromatography method is selected from the group consisting of silica gel chromatography, cellulose chromatography, ion-exchange chromatography, reverse phase chromatography, gel filtration chromatography, and florisil chromatography.

Yet another embodiment of the claimed invention is a process for preparing a 7,11 disubstituted Camptothecin derivative having the formula:

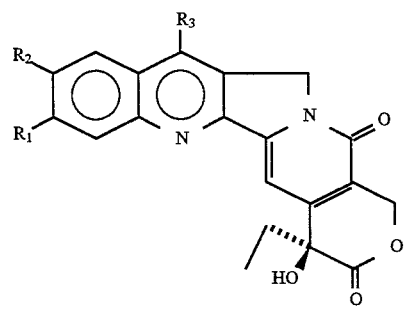

wherein R1 represents hydroxyl; wherein R2 represents hydrogen; wherein R3 represents a lower alkyl group, an alkylhydroxyl group,an alkylaroxylgroup, an acyloxy derivative, or a substituted alkyl aromatic group; and wherein the process comprises the following steps: a) suspend 11-Hydroxy Camptothecin in water; b) add ferrous salt and stir well; c) add an aldehyde, a carboxylic acid or an alcohol; d) add a volatile carboxylic acid at low temperature; e) add a suitable free radical generator; and f)isolate 7,11 disubstituted Camptothecin using a suitable chromatography method.

This claimed process is further defined wherein the aldehyde is propionaldehyde, the ferrous salt is iron sulfate heptahydrate, the volatile carboxylic acid is trifluoroacetic acid, the suitable free radical generator is selected from the group consisting of potassium persulfate and ammonium persulfate and the chromatography method is selected from the group consisting of silica gel chromatography, cellulose chromatography, ion-exchange chromatography, reverse phase chromatography, gel filtration chromatography, and florisil chromatography.

This invention is further defined as a process for preparing 11-Hydroxy-7-Ethyl Camptothecin having the formula:

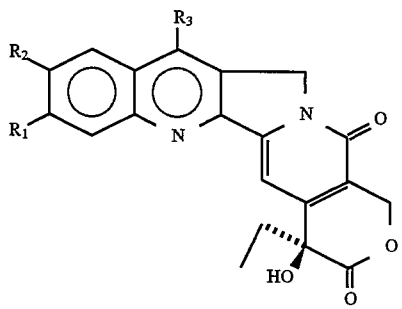

wherein R1 represents an hydroxyl; wherein R2 represents hydrogen; wherein R3 represents ethyl; and wherein the process comprises the following steps: a) suspend 11-Hydroxy Camptothecin in water; b)add ferrous salt and stir well; c) add an aldehyde, a carboxylic acid or an alcohol; d) add a volatile carboxylic acid at low temperature; e) add a suitable free radical generator; and f)isolate 11-Hydroxy-7-Ethyl Camptothecin using a chromatography method.

Another embodiment of this invention involves the direct administration of 11,7-HECPT or 11,7-HMCPT to human patients with cancer. Direct administration of 11,7-HECPT or 11,7-HMCPT is likely to offer several important clinical advantages over administration of CPT-11:

(1) direct administration of 11,7-HECPT or 11,7-HMCPT allows the clinician to tailor administration of active cytotoxic species to suit the patient's tolerance;

(2) direct administration of 11,7-HECPT or 11,7-HMCPT overcomes interpatient variability which may be due to polymorphism of key enzyme(s) in the metabolism of water soluble product forms of camptothecin such as CPT-11; and (3) clinicians can more consistently optimize the drug dosage and schedule to achieve the maximum tolerated dose of 11,7-HECPT or 11,7-HMCPT which is likely to lead to the most beneficial clinical anti-cancer effect.

Both 11,7-HECPT and 11,7-HMCPT can be used for the treatment of human cancers in the following ways:

(1) methods of administering 11,7-HECPT or 11,7-HMCPT to patients with cancer;

(2) solutions of 11,7-HECPT or 11,7-HMCPT;

(3) antitumor compositions comprising 11,7-HECPT or 11,7-HMCPT;

(4) stable formulations of 11,7-HECPT or 11,7-HMCPT suitable for parenteral administration;

(5) pharmacologic schedules for achieving the maximum tolerated dose with acceptable clinical toxicity observed in standard clinical practice of cancer treatment (<10% Grade 3 Toxicity by WHO Classification);

(6) a novel oral formulation of 11,7-HECPT or 11,7-HMCPT; and (7) use of 11,7-HECPT or 11,7-HMCPT for the treatment of localized complications of cancer by direct administration via instillation into various body cavities.

11,7-HECPT and 11,7-HMCPT Dissolved in DMI or DMA and Acid

An embodiment of the claimed invention is an 11-hydroxy-7-ethyl camptothecin (11,7-HECPT) or 11-hydroxy-7-methoxy camptothecin (11,7-HMCPT) solution comprising 11,7-HECPT or 11,7-HMCPT dissolved in dimethylisosorbide in the presence of a pharmaceutically acceptable acid or dissolved in dimethylacetamide in the presence of a pharmaceutically acceptable acid.

The 11-hydroxy-7-ethyl camptothecin or 11-hydroxy-7-methoxy camptothecin (11,7-HECPT and 11,7-HMCPT) solution is prepared by dissolving the desired components in dimethylisosorbide (DMI) or dimethylacetamide (DMA). Dimethylisosorbide has been used as solvent for muscle relaxants (U.S. Pat. No. 3,699,230), tetracyclines (U.S. Pat. No. 3,219,529), aspirin (U.S. Pat. No. 4,228,162), and steroids (U.S. Pat. No. 4,082,881 ). DMI and DMA have very good toxicity profiles and are miscible with ethanol, propylene glycol, isopropyl myristate, water, diethyl ether, corn oil, acetone, cottonseed oil, and the like. An object of the present invention is to provide a solution of 11,7-HECPT in DMI or DMA. A concentrated solution is particularly useful as a filling solution for gelatin capsules. The solution may also be formulated for parenteral use providing a useful and practical means to dissolve the drug. The present invention is prepared by dissolving the desired components in DMI or DMA and the resulting solution is then filtered and the filtrate collected. The amount of 11,7-HECPT or 11,7-HMCPT contained in the solution of this invention is not specifically restricted but may be any amount convenient for pharmaceutical purposes, and may be selected according to the dosage from to be prepared. A preferred capsule filling solution contains from about 0.1 mg to about 10.0 mg of 11,7-HECPT or 11,7-HMCPT activity per ml of solution.

Solutions of 11,7-HECPT or 11,7-HMCPT and Pharmaceutical Formulations Thereof

As a preferred embodiment of the claimed invention, an antitumor composition is prepared by dissolving a solution of 11-hydroxy-7-ethyl camptothecin or 11-hydroxy-7-methoxy camptothecin (11,7-HECPT or 11,7-HMCPT) in dimethylisosorbide (DMI) or dimethylacetamide (DMA) in the presence of a pharmaceutically acceptable acid.

As general information, a pharmaceutically acceptable acid is preferably included in the solutions of the present invention. Any pharmaceutically acceptable acid may be used; for example mineral acids such as hydrochloric acid; and organic carboxylic acids, such as tartaric, citric, succinic, fumaric, or maleic acids. An organic carboxylic acid is preferred, and citric acid is most preferred. The amount used may be from about 0.005 to about 0.5 parts by weight of acid per part by weight of 11,7-HECPT or 11,7-HMCPT and preferably from about 0.01 to 0.3 part by weight of acid per part by weight of 11,7-HECPT or 11,7-HMCPT. Citric acid is preferably used in a proportion of from about 0.05 to about 0.1, and about 0.1 part by weight in the presence of taurocholic acid or a pharmaceutically acceptable salt thereof.

In the formulations provided by the instant invention, the 11,7-HECPT or 11,7-HMCPT are both soluble and maintained in its active form. The non-enzymatic conversion of the pH labile E ring from the closed lactone (active) to the open carboxylate form (inactive) is reduced by formulating 11,7-HECPT or 11,7-HMCPT under acidic pH conditions (<5.0). A water soluble acid is included in this composition to assure that an acidic pH value is maintained upon dilution to form the micellar solution. Examples of preferred solid water soluble organic carboxylic acids which can be used include citric, gluconic, maleic, tartaric, or ascorbic acids. Other acids may be employed, but most preferred is citric acid.

A further embodiment of this invention is where the acid is an organic carboxylic acid. As stated above, there are a variety of different acids that would apply to this invention but the inventors prefer citric acid.

Yet another embodiment of the claimed invention is that the solution of 11,7-HECPT or 11,7-HMCPT contains from about 0.1 mg to about 10.0 mg activity of 11-hydroxy-7-ethyl camptothecin or 11-hydroxy-7-methoxy camptothecin per ml of solution. This concentration would be effective for both oral and parenteral administration of 11,7-HECPT or 11,7-HMCPT.

Oral Administration of 11,7-HECPT or 11,7-HMCPT

When oral dosages are to be administered in a capsule form, it is clearly superior to have a concentrated solution of 11,7-HECPT or 11,7-HMCPT suitable for encapsulation within a soft or hard gelatin capsule. Concentrated solutions allow the preparation of capsules of smaller size which allows easier ingestion by the patient, and may also reduce the number of capsules to be swallowed. These factors are important in view of the generally poor condition of cancer patients.

Taurocholic acid, a bile acid, may enhance the intestinal absorption of the drug in certain patients. The present invention takes advantage of the discovery that taurocholic acid, or a pharmaceutically acceptable salt thereof, when included in a solution dosage composition with 11,7-HECPT or 11,7-HMCPT results in improved absorption of the drug following ingestion of the composition. It is believed that this is due to the formation of a micellar solution of 11,7-HECPT or 11,7-HMCPT on dilution thereof with the gastric contents. The phenomenon of micellar solubilization of poorly water-soluble drugs mediated by bile acids, including taurocholic acid, has been previously reported with respect to glutethimide, hexesterol, griseofulvin, (Bates et al., Journal of Pharmaceutical Sciences, 55, 191–199), reserpine, Malone et al, ibid. 55, 972974 (1966), fatty acids and cholesterol (Westergaard et al., Journal of Clinical Investigation, 58, 97–108 (1976)).

The use of taurocholic acid or a pharmaceutically acceptable salt thereof in the present invention involves a pharmaceutical solution of 11,7-HECPT or 11,7-HMCPT which has the unique property of providing a stable apparent solution of the drug upon dilution thereof with from 1 to 100 volumes of water. The solution is stable and free of precipitate for a period of at least two hours sufficient to permit administration to and absorption by the mammalian organism. It has been observed with similar solutions of a different insoluble anticancer drug, etoposide, that the bioavailability of the drug following oral administration of a similar form is substantially equivalent to that achieved by intravenous administration of a solution of etoposide (U.S. Pat. No. 4,713,246). Analogous to that of etoposide, it is believed that ingestion of the present dosage form of 11,7-HECPT or 11,7-HMCPT and resulting dilution thereof by the stomach contents results in the formation of a micellar solution of 11,7-HECPT or 11,7-HMCPT in the stomach which is readily absorbed by the gastrointestinal tract. Applicants do not wish to be bound, however, by any theoretical explanation of the mechanism by which the superior oral bioavailability of the present 11,7-HECPT or 11,7-HMCPT formulation is achieved.

Antitumor Compositions Comprising 11,7-HECPT or 11,7-HMCPT

A preferred embodiment of the claimed invention is an antitumor composition comprising a solution of 11-hydroxy-7-ethyl camptothecin or 11-hydroxy-7-methoxy camptothecin dissolved in dimethylisosorbide or dimethylacetamide containing from about 0.1 mg to about 15.0 mg of 11-hydroxy-7-ethyl camptothecin or 11-hydroxy-7-methoxy camptothecin activity per ml and containing from about 0.01 to about 0.9 part by weight of a pharmaceutically acceptable organic carboxylic acid per part by weight of 11-hydroxy-7-ethyl camptothecin or 11-hydroxy-7-methoxy camptothecin.

An additional embodiment is wherein said part by weight of a pharmaceutically organic carboxylic acid is from about 0.05 to about 0.1 part by weight per part by weight of 11-hydroxy-7-ethyl camptothecin or 11-hydroxy-7-methoxy camptothecin and more preferably the acid is citric acid.

Another embodiment of this invention is an antitumor composition comprising a solution of 11-hydroxy-7-ethyl camptothecin or 11-hydroxy-7-methoxy camptothecin dissolved in dimethylisosorbide or dimethylacetamide in the presence of a pharmaceutically acceptable acid, wherein said solution further comprises taurocholic acid or a pharmaceutically acceptable salt thereof, and polyethylene glycol. Water is an optional ingredient to this composition.

Yet another embodiment of this invention is wherein said the solution of the antitumor composition contains for each part by weight of 11-hydroxy-7-ethyl camptothecin or 11-hydroxy-7-methoxy camptothecin, 1–10 parts by weight of dimethylisosorbide or dimethylacetamide, 0.005–0.5 parts by weight of a pharmaceutically acceptable acid, 1–10 parts by weight of taurocholic acid or a pharmaceutically acceptable salt thereof, and 1–10 parts by weight of polyethylene glycol. An additional embodiment is wherein said acid is an organic carboxylic acid and the inventors prefer citric acid. Of interest, if water is included in the composition 0.1–2.0 parts by weight water may be added.

Another embodiment of the claimed invention wherein the antitumor composition further comprises a lower alcohol. Many different alcohols would be effective in this invention, but the inventors prefer to use ethanol.

Another embodiment of the claimed invention wherein the antitumor composition further comprises glycerin as a cosolvent.

Yet another embodiment of this invention is an antitumor composition comprising a solution of 11-hydroxy-7-ethyl camptothecin or 11-hydroxy-7-methoxy camptothecin dissolved in dimethylisosorbide or dimethylacetamide in the presence of a pharmaceutically acceptable add, wherein said solution further comprises taurocholic acid or a pharmaceutically acceptable salt thereof, polyethylene glycol, ethanol, glycerin, and a buffer. Water is an optional ingredient to this composition.

An additional embodiment of this invention is wherein said solution contains for each part by weight of 11-hydroxy-7-ethyl camptothecin or 11-hydroxy-7-methoxy camptothecin, 1–10 parts by weight of dimethylisosorbide or dimethylacetamide, 0.005–0.5 parts by weight of a pharmaceutically acceptable acid, 1–10 parts by weight of taurocholic acid or a pharmaceutically acceptable salt thereof, 1–10 parts by weight of polyethylene glycol, 0.1–2 parts by weight of glycerin, 0.1–2 parts by weight of ethanol, and 0.005–0.5 parts of a buffer to maintain an acidic pH. Sodium acetate is an example of the buffer that can be used in the claimed composition. Optionally, this solution may also contain approximately up to 2.0 parts by weight water.

Another embodiment of this invention is wherein said polyethylene glycol has a molecular weight of about 300 and the antitumor composition further comprises a non-ionic surfactant. There are many different surfactants but the inventors prefer a poloxamer. Several different poloxamer's are available, for example, poloxamer 407 and PF-127. The inventors prefer to use PF-127 in the claimed invention.

Yet another embodiment of this invention is an antitumor composition comprising a solution of 11-hydroxy-7-ethyl camptothecin or 11-hydroxy-7-methoxy camptothecin dissolved in dimethylisosorbide or dimethylacetamide in the presence of a pharmaceutically acceptable acid, wherein said solution further comprises a lower alcohol, polyethylene glycol, and surfactant.

As a more preferred embodiment for this antitumor composition, the pharmaceutically acceptable organic acid is citric acid, wherein said polyethylene glycol has a molecular weight of about 300, wherein said lower alcohol is ethanol and wherein said surfactant is polysorbate-80.

Another embodiment of this invention is an antitumor composition comprising a solution of about 0.1 mg to about 15.0 mg of 11-hydroxy-7-ethyl camptothecin or 11-hydroxy-7-methoxy camptothecin dissolved in 1 to 10 parts of dimethylisosorbide or dimethylacetamide in the presence of about 0.1 to 0.5 parts of a pharmaceutically acceptable organic carboxylic acid, wherein said solution further comprises about 5 to 9 parts by weight of polyethylene glycol, about 0.1 to 2.0 parts of a pharmaceutically acceptable alcohol, and about 1 to 10 parts of a non-ionic surfactant.

More preferred for this antitumor composition is wherein the acid is citric acid, and the polyethylene glycol has a molecular weight of about 300, and the alcohol is ethanol and the surfactant is polysorbate-80.

Another embodiment of this invention is an antitumor composition comprising a solution about 0.1 mg to about 15.0 mg of 11-hydroxy-7-ethyl camptothecin or 11-methoxy-7 ethyl camptothecin dissolved in 1 to 10 parts of dimethylisosorbide or dimethylacetamide in the presence of 0.1 to 0.5 parts of a pharmaceutically acceptable organic carboxylic acid, wherein said solution further comprises about 0.1 to 2.0 parts of a pharmaceutically acceptable alcohol, and about 1 to about 10 parts of a non-ionic surfactant.

More specifically, the acid is citric acid, and the alcohol is ethanol, and the non-ionic surfactant is comprised of polyoxyethylated castor oil. (Cremaphor EL™)

Another embodiment of this invention is an antitumor composition comprising a solution of 0.1 mg to about 15.0 mg of 11-hydroxy-7-ethyl camptothecin or 11-methoxy-7-ethyl camptothecin dissolved in 1 to 10 parts of dimethylisosorbide or dimethylacetamide, wherein said solution further comprises about 1 to 10 parts polyoxyethylated castor oil, about 0.1 to 2 parts by weight dehydrated ethyl alcohol USP, and about 0.1 to 0.9 parts citric acid.

In a more preferred embodiment, 11,7-HECPT or 11,7-HMCPT is solubilized in a manner suitable for clinical use by forming a sterile, nonaqueous solution of 1 part of 11,7-HECPT or 11,7-HMCPT per 1 to 3 ml in a vehicle comprising dehydrated ethyl alcohol 0.1–2.0 parts by weight, benzyl alcohol 0.1–2.0 parts by weight, citric acid 0.1–0.9 parts by weight, polyethylene glycol 200–300 4 to 10 parts by weight, and polysorbate-80 (Tween 80) 1 to 10 parts, dimethylisosorbide 1 to 10 parts in acidified medium with a pH of 3 to 4. This preferred embodiment of an 11,7-HECPT or 11,7-HMCPT solution in dimethylisosorbide or dimethylacetamide is summarized in the table as follows:

| INGREDIENTS | PARTS BY WEIGHT |
| --- | --- |
| 11-Hydroxy-7-Ethyl Camptothecin or 11-Hydroxy-7-Methoxy Camptothecin | 1 |
| EtOH | 0.1–2.0 |
| Benzyl Alcohol | 0.1–2.0 |
| Citric Acid | 0.1–0.9 |
| PEG 300 | 4–10 |
| Dimethylisosorbide or dimethylacetamide | 1–10 |
| Polysorbate 80 (Tween-80) | 1–10 |

Another more preferred parenteral formulation comprises 11,7-HECPT or 11,7-HMCPT formulated for dilution prior to parenteral administration made of 1 part 11,7-HECPT or 11,7-HMCPT in 2 ml of nonaqueous solvents including 1 to 10 parts Cremaphor EL™ (polyoxyethylated castor oil), 0.1 to 2 parts dehydrated ethyl alcohol USP, dimethylisosorbide dimethylacetamide 1 to 10 parts, and citric acid 0.1–0.9 parts to adjust the final pH to between 3 to 4.

This preferred embodiment of an 11,7-HECPT or 11,7-HMCPT solution in dimethylisosorbide or dimethylacetamide is as follows:

| INGREDIENTS | PARTS BY WEIGHT |
| --- | --- |
| 11-Hydroxy-7-Ethyl Camptothecin or 11-Hydroxy-7-Methoxy Camptothecin | 1 |
| Cremaphor EL ™ | 1–10 |
| EtOH | 0.1–2.0 |
| Citric Acid | 0.1–0.9 |
| Dimethylisosorbide or dimethylacetamide | 1–10 |

Dosages and Schedules for Parenteral Administration of 11,7-HECPT or 11,7-HMCPT Compositions Another embodiment of this invention is a method of administration of 11,7-HECPT or 11,7-HMCPT to a patient with cancer comprising infusing a fixed amount of 11,7-HECPT or 11,7-HMCPT over a period of time and repeated at predetermined intervals. For the purpose of this invention, 11,7-HECPT is meant to include both 11,7-HECPT and 11,7-HMCPT.

A more specific embodiment of the claimed invention is a method for administration of 11,7-HECPT or 11,7-HMCPT to a patient with cancer comprising infusing from about 1.0 mg/m$^2$ to about 33.0 mg/m$^2$ of said compound over a duration of approximately 120 minutes every 21 to 28 days.

An additional embodiment of the claimed invention is a method for administration of 11,7-HECPT or 11,7-HMCPT to a patient with cancer comprising infusing from about 1.0 mg/m$^2$ to about 16.0 mg/m$^2$ of said compound over a duration of approximately 120 minutes for three consecutive days every 21 to 28 days.

Another embodiment of the claimed invention is a method for administration of 11,7-HECPT or 11,7-HMCPT to a patient with cancer comprising infusing from about 1.0 mg/m$^2$ to about 20.0 mg/m$^2$ of said compound over a duration of approximately 120 minutes given once per week for three consecutive weeks with 2 weeks rest after each 3 week cycle.

Another embodiment of the claimed invention is a method for administration of 11,7-HECPT or 11,7-HMCPT to a previously untreated patient with cancer comprising infusing from about 1.0 mg/m$^2$ to about 24.0 mg/m$^2$ of said compound over a duration of approximately 120 minutes given once per week for three consecutive weeks with 2 weeks rest after each 3 week cycle.

Yet another embodiment of the claimed invention is a method for administration of 11,7-HECPT or 11,7-HMCPT to a patient with cancer comprising continuously infusing from about 0.1 mg/m²/d to about 6.0 mg/m²/d of said compound over a duration of approximately 24 to 120 hours every 21 to 28 days.

Another embodiment of this invention wherein the 11,7-HECPT or 11,7-HMCPT is infused into a patient with cancer is that the 11,7-HECPT or 11,7-HMCPT is dissolved in dimethylisosorbide (DMI) or dissolved in dimethylacetamide (DMA) in the presence of a pharmaceutically acceptable acid.

Dosages and Schedules for Oral Administration of 11,7-HECPT or 11,7-HMCPT Compositions Another embodiment of this invention is a method of oral administration of 11,7-HECPT or 11,7-HMCPT to a patient with cancer comprising an amount of 11,7-HECPT or 11,7-HMCPT and given as a single dose or divided into smaller doses over a specified amount of time and repeated after a fixed amount of time.

More specifically, another embodiment of this invention is a method for oral administration of 11,7-HECPT or 11,7-HMCPT to a patient with cancer comprising administering from about 2.5 mg/m² to about 100 mg/m² of said compound in single or divided dosages within a 24 hour period every 21 to 28 days.

Yet another embodiment of this invention is a method for oral administration of 11,7-HECPT or 11,7-HMCPT to a patient with cancer comprising administering from about 1.0 mg/m² to about 50 mg/m² of said compound daily in single or divided doses for three consecutive days every 21 to 28 days.

Another embodiment of this invention is a method for oral administration of 11,7-HECPT or 11,7-HMCPT to a patient with cancer comprising administering from about 1.0 mg/m² to about 60.0 mg/m² of said compound in single or divided dosages within a 24 hour period given once per week for three consecutive weeks with 2 weeks rest after each 3 week cycle.

Another embodiment of this invention is a method for oral administration of 11,7-HECPT or 11,7-HMCPT to a previously untreated patient with cancer comprising administering from about 2.0 mg/m² to about 75 mg/M² of said compound in single or divided doses within a 24 hour period once per week for three consecutive weeks with 2 weeks rest after each 3 week cycle.

For the purpose of this invention, a previously unrelated patient is defined as a patient with cancer who has not previously been treated with any chemotherapeutic drugs.

An additional embodiment of this invention is a method for oral administration of 11,7-HECPT or 11,7-HMCPT to a patient with cancer comprising administering from about 0.5 mg/m²/d to about 18.0 mg/m²/d of said compound in single or divided daily doses administered within each 24 hour period for two to five consecutive days and repeated every 21 to 28 days.

Yet another embodiment of this invention for oral administration to a patient with cancer is 11,7-HECPT or 11,7-HMCPT dissolved in dimethylisosorbide (DMI) or dimethylacetamide (DMA) in the presence of a pharmaceutically acceptable acid. More specifically, approximately 10 mg of 11,7-HECPT or 11,7-HMCPT can be dissolved in each milliliter of DMA. However, only approximately 5.0 mg of 11,7-HECPT or 11,7-HMCPT can be dissolved in each milliliter of DMI.

A further embodiment of this invention is the claimed composition and method of administering the composition by encapsulating the claimed formulations within a hard gelatin capsule. Yet another embodiment of the claimed composition and method of administering the composition is encapsulating the claimed formulations within a soft gelatin capsule. One of ordinary skill in the art will know that any of the claimed formulations adapted for oral administration can be used as the fill for the soft or hard gelatin capsule.

A more specific embodiment of the claimed invention is an oral formulation of 11,7-HECPT or 11,7-HMCPT in soft gelatin capsules (comprised of gelatin/glycerin/sorbitol/purifiers/purified water) containing 1.0 part of 11,7-HECPT or 11,7-HMCPT in a vehicle comprising citric acid 0.1 to 0.9 parts by weight, purified water 1 part by weight, glycerin 1 to 10 parts by weight, and polyethylene glycol 200 to 300 5 to 9 parts by weight, dehydrated ethyl alcohol 10 to 20% by weight of total solution weight, sodium acetate 0.05 to 0.5 parts by weight, a surfactant, and dimethylisosorbide or DMA 1 to 10 parts. A more preferred oral formulation will include pluronic F-127 poloxamer as a surfactant using 0.05 to 1.0 parts by weight, and Cremaphor EL™ using 1–10 parts by weight of Cremaphor EL™.

A more preferred oral formulation will include the addition of taurocholic acid 2 to 10 parts by weight. The soft gelatin capsules may also be composed of any of a number of compounds used for this purpose including, for example, a mixture of gelatin, glycerin, sorbitol, purified water, and parabens.

The Table below indicates parts by weight of different components to be included in the oral formulation to be administered in capsules. Several components are marked as "optional" (purified water, glycerin, poloxamer surfactant, tautocholic acid and Cremaphor EL™). Inclusion of these components depends on a variety of different factors; i.e. type of cancer the patient has, pretreated previously, etc. For the purpose of this invention, Cremaphor EL™ is polyoxyethylated castor oil.

| INGREDIENTS | PARTS BY WEIGHT |
| --- | --- |
| 10-Hydroxy-7-Ethyl camptothecin or 11-Hydroxy-7-Methoxy camptothecin | 1 |
| Citric Acid | 0.1–0.5 |
| Purified Water (Optional) | 0.5–1.5 |
| Glycerin (Optional) | 0.4–2 |
| PEG 300 | 5–9 |
| EtOH (Optional) | 10–20% by weight of total solution weight |
| Dimethylisosorbide or dimethylacetamide | 1–10 |
| Poloxamer surfactant (Optional) | 0.05–1.0 |
| Sodium Acetate | 0.05–0.5 |
| Taurocholic Acid (Optional) | 2–10 |
| Cremaphor EL ™ (Optional) | 1–10 |

Clinicians will administer 11,7-HECPT or 11,7-HMCPT to human patients with cancer according to schedules that maximize its potential antitumor effects and diminish its potential toxic side effects. The antitumor activity of 11,7-HECPT or 11,7-HMCPT is increased to a much greater degree by increasing the duration of exposure (time dependent) than increases observed with increasing the dosages (dose dependent) of the drug, except at extremely high doses which produce high plasma concentrations of the drugs. The greater antitumor effects associated with increasing the duration of exposure is a finding that is most likely related to the predominant S-phase mode of antitumor activity of 11,7-HECPT or 11,7-HMCPT. 11,7-HECPT or 11,7-HMCPT are S-phase-active agents; therefore, the greatest antitumor effect in humans will likely be observed with longer infusion or closely spaced repetitive administration schedules. Such schedules of administration would expose more cycling tumor cells to the drug and increase the frequency of exposure of the tumor cells in S-phase to sufficiently toxic levels of the drug.

Another preferred embodiment of the present invention is a separation methodology for 10-hydroxy camptothecin and 11-hydroxy camptothecin from a mixture using a SOXHLET apparatus. The procedure does not involve any acid treatment or workup procedure and the solvent of choice is pharmaceutically acceptable ethyl alcohol USP (absolute-200 proof).

A further embodiment of this invention is that the claimed 11,7-HECPT or 11,7-HMCPT composition or claimed 11,7-HECPT or 11,7-HMCPT dissolved in DMI or dissolved in DMA can be used in a variety of different cancer types. The claimed formulations and compositions of the invention may be used in treatment of a number of tumors including, without limitation, human cancers of the lung, breast, colon, prostate, melanoma, pancreas, stomach, liver, brain, kidney, uterus, cervix, ovaries, and urinary tract.

The site and type of tumor to be treated will, in many cases, influence the preferred route of administration and therapeutic regimen to be applied. Consequently, although the formulations of the invention may be most usually be administered by intravenous injection or infusion, they also be delivered directly into the tumor site or by other methods designed to target the drug directly to the tumor site. For example, in patients with malignant pleural effusion, the intrapleural route, may be preferred; in patients with poor venous access the subcutaneous route of administration may be preferred; in patients with primary or metastatic cancer involving the brain or nervous system, the intracisternal or intrathecal route of administration may be most advantageous; in patients with malignant ascites secondary to cancer, one may select intraperitoneal administration; and in patients with bladder cancer direct intravesicular instillation may be most advantageous. Similarly, in tumors of the skin, the formulation may be topically applied. An oral formulation is also provided for use where suitable.

Thus, an additional embodiment of this invention is that the claimed 11,7-HECPT solution comprising 11,7-HECPT dissolved in DMI or DMA, in the presence of a pharmaceutically acceptable acid, is sterilized and prepared for oral, intrapleural, intrathecal, subcutaneous, intracisternal, intravesicular, intraperitoneal, topical or parenteral administration to a patient with cancer.

Thus, an additional embodiment of this invention is that the claimed 11,7-HMCPT solution comprising 11,7-HMCPT dissolved in DMI or DMA, in the presence of a pharmaceutically acceptable acid, is sterilized and prepared for oral, intrapleural, intrathecal, subcutaneous, intracisternal, intravesicular, intraperitoneal, topical or parenteral administration to a patient with cancer.

The formulations of the claimed invention may also be used in conjunction with other drugs in methods of convergent therapy whereupon an additional drug or drugs are coadministered along with the claimed 11,7-HECPT or 11,7-HMCPT composition. Thus, 11,7-HECPT or 11,7-HMCPT may be co-administered with CPT-11, topotecan, camptothecin, or 10,11-methylenedioxy camptothecin, using a pharmaceutically acceptable carrier, and wherein the co-administration is based on an optimal dosage and schedule. For example, in a preferred embodiment, CPT-11 may be co-administered with 11,7-HECPT or 11,7-HMCPT. Also, 11,7-HECPT or 11,7-HMCPT may co-administered with a combination of CPT-11, topotecan, camptothecin, and 10,11-methylenedioxy camptothecin, using a pharmaceutically acceptable carrier, and wherein the co-administration is based on an optimal dosage and schedule. For example, in a preferred embodiment, CPT-11 and topotecan may be co-administered with the claimed 11,7-HECPT or 11,7-HMCPT.

A further embodiment is a method of treatment of cancer in humans with convergent therapy or combination therapy. This claimed method dissolves the compound 11-hydroxy-7-ethyl camptothecin or 11-methoxy-7-ethyl camptothecin in dimethylisosorbide (DMI) or dimethylacetamide in (DMA), in the presence of pharmaceutically acceptable acid and co-administers it with additional drugs selected from the group consisting of, but not limited to, carmustine, azathioprine, cis-platinum, carboplatin, iproplatin, DTIC, cyclophosphamide, ifosfamide, etoposide, ara-C, doxorubicin, daunorubicin, nitrogen mustard, 5-fluorouracil, bleomycin, mitomycin-C, fluoxymesterone, mechlorethamine, teniposide, hexamethylmelamine, leucovorin, melphelan, methotrexate, mercaptopurine, mitoxantrone, BCNU, CCNU, procarbazine, vincristine, vinblastine, vindesine, thioTEPA, amsacrine, G-CSF, GM-CSF, erythropoietin, γ-methylene-10-deazaminopterin, γ-methylene-10-ethyl-10-deazaaminopterin, taxol, and 5-azacytidine. For the purpose of this invention, the terms convergent, co-administered, and combination are used interchangeably.

11,7-HECPT or 11,7-HMCPT in DMI or DMA when administered parenterally, is preferably diluted with an appropriate volume of a parenteral vehicle to a concentration of about 0.1 mg/ml or lower of 11,7-HECPT or 11,7-HMCPT activity. A further embodiment of the claimed invention is a sterile solution of any of the claimed 11,7-HECPT or 11,7-HMCPT compositions and formulations for sterile administration to a patient with cancer upon dilution with a sterile parenteral vehicle. For the purposes of this invention, parenteral vehicles include dextrose 5 to 10% in water, 0.9% NaCl in water with or without 5% or 10% Dextrose, 0.45% NaCl in water with or without 5% or 10% Dextrose, and 3% NaCl in water with or without 5% to 10% Dextrose, or sterile lipid formulations, such as intralipid, used for parenteral nutritional support for cancer patients.

EXAMPLES

The following examples illustrate selected modes for carrying out the invention and are not to be construed as limiting the specification and claims in any way.

Isolation of Individual Camptothecin Derivatives

This invention describes a reliable and commercially useful convergent process for synthesizing hydrophobic camptothecin derivatives possessing significant antitumor activity. The claimed method uses commercially available mixtures of 11-hydroxy and 10-hydroxy camptothecin, which can be purchased commercially. This mixture is comprised of 10-hydroxy camptothecin and 11-hydroxy camptothecin in an approximate ratio of 2:1 as natural isolates. Large quantities of the naturally available mixture of 10-hydroxy camptothecin and 11-hydroxy camptothecin (approximate ratio of 2:1) can be effectively separated into the two component products (10-hydroxy camptothecin and 11-hydroxy camptothecin) by the following two procedures.

A. Separation of 10-Hydroxy Camptothecin and 11-Hydroxy Camptothecin Using silica Gel Liquid Chromatography Microscale separation of 10-hydroxy camptothecin and 11-hydroxy camptothecin starting with the aforementioned commercially available mixture is performed by using 2 mm thick silica gel thin layer chromatography plates. The 10-hydroxy camptothecin and 11-hydroxy camptothecin mixture is quartenized to trifluoroacetate salt by dissolving in the minimal amount of trifluoroacetic acid. The resulting homogeneous solution is then applied to a silica gel plate and initially eluted with wet 20% methanol in chloroform. For the purpose of this invention, quartenizing describes how weak organic bases, such as tertiary nitrogen atoms, can be converted to corresponding salts ionic in nature by treating a weak organic base with either a carboxylic acid or a mineral acid. The chromatographic plate is eluted vertically at atmospheric pressure using a mixture of methanol and chloroform, the typical corn position of which is 50% for each of the two solvents. The inventors observed that, under these conditions, the 11-hydroxy camptothecin component will migrate from the base line on the thin layer plate to an Rf value of approximately 0.38. This in direct contrast to the 10-hydroxy camptothecin, which under the same conditions, remains at the origin of the chromatogram. The 11-hydroxy camptothecin that has thus travelled upward the plate is recovered from the plate. Once the fast moving 11-hydroxy camptothecin is recovered, a second elution of the plate with a mixture of methanol, chloroform and triethylamine, the typical composition of which is 0.1% triethylamine in a 1:1 mixture of methanol and chloroform, causes the 10-hydroxycampothecin component to migrate upward the plate. The 10-hydroxycampothecin component may then be recovered from the plate.

To perform the purification on a gram scale, column chromatography is used to separate the 10-hydroxy camptothecin and 11-hydroxy camptothecin mixture into individual components of greater than 90% purity. Further purification to higher degrees of these camptothecin derivatives is accomplished by simple fractional crystallization using 75–80% chloroform in methanol.

Using the same methods, mono-substituted 10 and 11-acyloxy and alkoxy camptothecins or disubstituted CPT 7, 10, or 7, 11 derivatives can also be separated with a high degree of purity for each of the individual components.

B. Separation of 10-Hydroxy Camptothecin and 11 Hydroxy Camptothecin Using a Soxhlet Apparatus Additionally, large quantities of the naturally available mixture of 10-hydroxy camptothecin and 11-hydroxy camptothecin can be effectively separated into 10-hydroxy camptothecin and 11-hydroxy camptothecin by using a Soxhlet apparatus (Available from Ace Glass, Inc.; 1430 Northwest Boulevard, Vineland, N.J. 08360). This procedure does not either involve an acid treatment or does it involve any workup procedure. Another advantage of this separation method is that the solvent of choice is pharmaceutically acceptable ethyl alcohol USP (absolute 200 proof).

A typical separation methodology is as follows:

1. 1 gram of a mixture of 10-hydroxy CPT and 11-hydroxy CPT is placed into a thimble of a type suitable for use in a Soxhlet apparatus. The loaded thimble is introduced into a Soxhlet extractor of suitable capacity.

2. The Soxhlet extractor is connected to a suitable flask which contains 75 ml of absolute ethyl alcohol. The solvent is heated to reflux and the Soxhlet extraction is continued for 30 minutes.

3. The apparatus is then cooled to room temperature and the solvent is withdrawn in order to recover the 10-hydroxy camptothecin and in order to avoid prolonged heating of 10-hydroxy camptothecin that precipitates from the ethanolic solution.

4. Fresh ethyl alcohol is introduced and the process is repeated.

5. The ethanolic suspension of 10-hydroxy camptothecin obtained as described in step 3 above is analyzed for the presence of 10-hydroxy camptothecin by thin layer chromatography techniques.

6. Ethanol is completely removed in vacuo from the ethanolic suspension of 10-hydroxy camptothecin obtained as described in step 3 by the use of a rotary evaporator. The residue is determined to be 10-hydroxy camptothecin of greater than 95% purity. 10-Hydroxy camptothecin can thus be purified with about a 80% recovery. The isolated 10-hydroxy camptothecin is then easily recrystallized from a solvent mixture of typical composition 85% chloroform—15% methanol.

7. The insoluble portion remaining in the Soxhlet thimble is then dried and analyzed separately. This insoluble portion is found to be 11-hydroxy camptothecin of approximately 90% purity. This fraction can be pooled from different batches to obtain subcrops.

The purities of the recovered products are determined by comparing the spectral and analytical data with those of authentic samples of 10 and 11-hydroxy camptothecins.

Example 1

Separation of 11-Hydroxy Camptothecin

Naturally available mixture of 10 and 11-hydroxy camptothecin (1.0 g) is dissolved in anhydrous trifluoroacetic acid (5 ml) and anhydrous methanol (10 ml) to form a homogeneous solution of the quartenized components of the mixture. The homogeneous solution is then absorbed over enough silica gel (60A; 60–230 mesh) to form a thick slurry. This slurry is dried by evaporating the methanol and excess acid in vacuo on a rotary evaporator, leaving a powdery mass. The powder is then loaded over a pre-equilibrated silica gel column using chloroform. The column is washed using 500 ml of chloroform to remove non polar impurities and occluded trifluoroacetic acid. Elution is accomplished with a solvent mixture of 80% chloroform-20% methanol. Using this eluent, the band migrating away from the origin is collected (Fraction A). Evaporation of the solvents is analyzed to be pure 11-hydroxy camptothecin.

1H NMR (DMSO-d6); 0.88 $\delta$(3H, t, J=7 Hz); 1.29 $\delta$(2H, q, J=5.2 Hz); 5.21 $\delta$(2H, m); 6.51 $\delta$(1H, s); 7.25 $\delta$(2H, m); 7.35 $\delta$(2H, m); 7.9 $\delta$(1Hd, J=5.4 Hz); 8.45 $\delta$(1H, s).

13C NMR: 87.3, 29.3, 49.6, 64.7, 71.09, 95.8, 102.7, 118.0, 120.4, 124.6, 144.7, 145.6, 156.5, 158.4, 200.2

FAB MS: 165.1 $(M+1)^+$

Example 2

Separation of 10-Hydroxy Camptothecin

Naturally available mixture of 10 and 11-hydroxy camptothecin (1.0 g) is dissolved in anhydrous trifluoroacetic acid (5 ml) and anhydrous methanol (10 ml) to form a homogeneous solution of the quaternized components of the mixture. The homogeneous solution is then absorbed over enough silica gel (60A; 60–230 mesh) to form a thick slurry. This slurry is dried by evaporating methanol and excess acid in vacuo on a rotary evaporator, leaving a powdery mass. The powder is then loaded over a pre-equilibrated silica gel column using chloroform. The column is washed using 1000 ml of a solvent mixture of 80% chloroform-20% methanol to remove non polar impurities, occluded trifluoroacetic acid and 11-hydroxycamptothecin (fraction A). Elution is then continued with chloroform-methanol-triethyl amine (in the approximate ratio of 1:1:0.01) and the band migrating away from the origin is collected using this eluent (Fraction B). Fractions A and B are evaporated separately and analyzed. Fraction B corresponds to the 10-hydroxy camptothecin isolate.

1H NMR (DMSO-d6); 0.88 δ(3H, τ, J=7 Hz); 1.27 δ(2H, q, J=5.2 Hz); 5.21 δ(2H, s); 5.41 δ(2H, m); 6.51 δ(1H, s); 7.25 δ(2H, m); 7.35 δ(2H, m); 8.09 δ(1H, d, J=5.4 Hz); 8.41 δ(1H, s).

$^{13}$C NMR: δ5 7.3, 29.3, 49.6, 64.7, 71.9, 95.8, 102.7, 118.0, 120.4, 124.8, 144.9, 145.9, 156.3, 158.4, 200.5

FAB MS: 165.1 (M+1)$^+$

Example 3

Preparation of 7,11-Substituted or 7,10-Substituted Camptothecin Using Two Different Methods The present invention teaches a novel process technology wherein purified hydroxy camptothecins described above are chemically transformed into corresponding hydroxy, 7-substituted camptothecins in a single step by regiospecific homolytic free radical mediated alkylation/acylation/hydroxymethylation without masking the phenolic moiety.

This novel method teaches a single step conversion of 10 or 11-substituted camptothecins to 10 or 11-substituted 7-substituted camptothecins. More specifically, this invention teaches the conversion of 11-hydroxy or 10-hydroxy camptothecin isolates to their respective 7-alkyl derivatives. In one step, the procedure described yields 7-alkyl-10 and 11 phenolic camptothecins, which are among the most active camptothecin derivatives.

To the inventors knowledge, single step alkylation of unprotected phenolic camptothecins has not been reported in the literature. The inventor's present two different methods for single step alkylation of unprotected phenolic camptothecins:

1. Method A: Using Trifluoroacetic Acid, Persulfate Salts, and Ferrous Salts

Using corresponding aldehydes, alcohols or carboxylic acids in presence of ferrous (i.e., Fe(II)) salts, suitable persulfate salts (i.e. potassium persulfate) and trifluoroacetic acid as solvent in molar equivalent quantity of concentrated sulfuric acid at a lower temperature during approximately 16 hour exposure time. However, the inventor's have found the addition of sulfuric acid is optional.

2. Method B. Using Hydrogen Peroxide, Sulfuric Acid, and Ferrous Salts (Fenton-type conditions)

Similar single step conversion is also performed using conventional Fenton-type reagents.

Method A: Trifluoroacetic Acid, Persulfate Salts, and Ferrous Salts

The present invention is far superior to the previously reported Fenton's reagent assisted alkylation of protonated nitrogen heterocycles, particularly quinolines. A high yielding and convergent synthetic methodology has tremendous synthetic significance due to the fact that alternative Friedel-Craft alkylations and acylations are not practical for most of the biologically relevant nitrogen heterocycles, and are also not practical for unprotected phenolic substrates in particular. The prior art analogous to the present invention includes acid catalyzed alkylation using carboxylic acids in the presence of silver nitrate, with sulfuric acid-water as solvents and hydrogen peroxide as a free radical generator.

Ammonium persulfate is rarely used as a promoter in alkylation of simple quinoline systems. Heterogeneous phases have also been investigated in order to reduce competitive reactions, such as decarboxylations, etc., and/or lack of regioselectivity. However, none of these methodologies are satisfactory for the alkylation of hydroxy camptothecins, for the following reasons. The strong acids that are required for the radical process will also cause protonation of the organic substrate and of the products of the reaction. Protonation of substrates/products is necessary in order to cause dissolution of these materials in the aqueous medium. However, the protonated products are difficult to extract from the aqueous acidic mixtures by the use of organic solvents, resulting in unsatisfactory recoveries. On the other hand, neutralization of the acid prior to product recovery causes precipitation of large quantities of inorganic salts that tend to absorb much product, and formation of very thick emulsions that are difficult to break up. These problems conspire to again provide unsatisfactory recoveries.

Method A has replaced strong mineral acids such as sulfuric acid or hydrochloric acid with trifluoroacetic acid (TFA), a volatile organic acid. The reaction is found to proceed smoothly in the presence of 1:1 TFA and water, with or without the presence of catalyic to mole ratio of sulfuric acid as co-catalyst. Hydrogen peroxide, a free radical generator with short shelf life (the substance degrades on storage and peroxide concentration drops significantly) is substituted with stable, commercially available, persulfate salts such as potassium persulfate. Additionally, persulfate salts are the free radical generators of choice in our system, because the formation of trifluoromethyl radicals, through decomposition of trifluoroacetic acid during the reaction, is effectively eliminated. Method A provides consistently high yield of desired product while greatly simplifying isolation of the products.

Method B: Hydrogen Peroxide, Sulfuric Acid, and Ferrous Salts

Method B involves hydrogen peroxide and ferrous salts as the free radical generator and aqueous sulfufic acid as the solvent. It has been shown that regiospecific alkylation of unprotected hydroxy quinoline systems can be performed under modified reaction conditions using appropriate alcohols, carboxaldehydes, or carboxylic acids as the alkylating agents. It was discovered that Fenton's reagent (hydrogen peroxide in presence of iron sulfate heptahydrate) or similar mixtures of hydrogen peroxide and ferrous salts, induce alkylation of 10 and 11-hydroxy camptothecins with the aforementioned alkylating agents in a highly regiospecific fashion, without the formation of undesired byproducts such as camptothecin-N-oxide or isomeric hydroxyl or alkyl derivatives of camptothecins. As reported for Minisci reactions (Minisci, et al.), the incoming alkyl group contains one carbon atom less than the starting alcohol or aldehyde or carboxylic acid, as the OH-bearing carbon atom (in the case of alcohols) or the carbonyl carbon (in the case of aldehydes and carboxylic acids) and is lost during the course of the reaction. Reactions where respective carboxaldehyde is used provides the maximum yield. In order to maintain homogenity and moderate reaction times, the solvent of choice is 50% sulfuric acid. However, at the end of the reaction, excess sulfuric acid must be destroyed by neutralizing the reaction mixture by slow addition of solid sodium bicarbonate. This neutralization step is important in order to extract out the product from the aqueous medium.

Example 4

Preparation of 10-Hydroxy-7-Ethyl Camptothecin Using Method A

The procedure for synthesizing 10-hydroxy-7-ethyl camptothecin using method A is as follows:

The 10-hydroxy camptothecin (800 mg; 2.2 mmol) is suspended in water (24 ml). Iron (II) sulfate heptahydrate (250 mg, 0.85 millimoles) is added to the suspension and then followed by the addition of propionaldehyde (3 ml). The reaction mixture is then cooled in an ice bath and concentrated sulfuric acid (1 ml) and trifluoroacetic acid (24 ml) are added. After stirring the homogeneous solution for 15 minutes, potassium persulfate (3.5 g; 6 mol equivalent) is added, and the mixture is slowly warmed to room temperature. After approximately 15 hours, the reaction mixture is diluted with water and the product is extracted using excess chloroform. The crude product is washed thrice with 5% methanol in ether and dried to obtain 806 mg of the desired compound.

$^1$H NMR (300 MHz; DMSO-d6): 0.87 δ(3H, t, J=7 Hz); 1.62 δ(3H, t, J=7 Hz); 1.85 δ(2H, 1 q, J=5 Hz); 3.18 δ(2H, q, J=5 Hz); 5.19 δ(2H, m); 5.40 δ(2H, s); 6.51 δ(1H, bs); 7.23 δ(2H, m); 7.39 δ(1H, d, J=10 Hz); 8.01 δ(1H, d, J=9 Hz)

$^{13}$C NMR: δ7.3, 13.6, 22.4, 29.8, 72.0, 95.8, 102.7, 117.9, 120.4, 124.8, 144.6, 145.3, 156.5, 158.3, 200.1

FAB MS: 403 (M+1)$^+$

Example 5

Preparation of 10 Hydroxy-7-Ethyl Camptothecin Using Method B

The procedure for synthesizing 10-hydroxy-7-ethyl camptothecin using Method B is as follows:

10-hydroxy camptothecin (3.0 g; 8.2 mmol) is suspended in water (75 ml) and iron (II) sulfate heptahydrate (0.87 g) is added. This solution is cooled in an ice-salt bath and stirred well. Propionaldehyde (12 ml)is introduced, followed by concentrated sulfuric acid (31 ml). Hydrogen peroxide (30%; 8 mole equivalents) is added in a dropwise manner at −10° C. The reaction mixture is then stirred for approximately 2.5 hours, during which time the mixture is slowly allowed to warm to room temperature. The dark brown colored reaction mixture is diluted with water (100 ml) and extracted once with ether (100 ml) to remove certain impurities. The aqueous solution is neutralized by the slow addition of solid sodium bicarbonate and extracted with excess 70% chloroform in methanol to recover the products. The combined extracts are dried over anhydrous sodium sulfate, concentrated and flash-chromatographed through a silica gel column using 10% methanol in chloroform as eluant. Final purification is performed by crystallization from 80% methanol in chloroform. Spectral and analytical data match those of an authentic sample.

$^1$H NMR (300 MHz; DMSO-d6): 0.87 δ(3H, t, J-7 Hz); 1.62 δ(3H, t, J=7 Hz); 1.85 δ(2H, 1q, J=5 Hz); 3.18 δ(2H, q, J=5 Hz); 5.19 δ(2H, m); 5.40 δ(2H, s); 6.51 δ(1H, bs); 7.23 δ(2H, m); 7.39 δ(1H, d, J=10 Hz); 8.01 δ(1H, d, J=9 Hz)

$^{13}$C NMR: δ7.3, 13.6, 22.4, 29.8, 72.0, 95.8, 102.7, 117.9, 120.4, 124.8, 144.6, 145.3, 156.5, 158.3, 200.1

FAB MS: 403 (M+1)$^+$

Example 6

Preparation 11-Hydroxy-7-Ethyl Camptothecin Using Method A

The procedure for synthesizing 11-hydroxy-7-ethyl camptothecin using method A is as follows: The hydroxy camptothecin (400 mg; 1.1 mmol) is suspended in water (12 ml). Iron (I) sulfate heptahydrate (220 mg) is added to the suspension and then propionaldehyde (1.5 ml) is added. The reaction mixture is then cooled in an ice bath and concentrated sulfuric acid (1 ml) and trifluoroacetic acid (12 ml) are added. After stirring the homogeneous solution for 15 minutes, potassium persulfate (2.0 g; 6 mole equivalents) is added and the mixture is allowed to slowly warm, to room temperature. After approximately 15 hours, the reaction mixture is diluted with water and the product is extracted using excess chloroform. The crude product is washed thrice with 5% methanol in either and dried to produce 350 mg of the desired material.

$^1$H NMR (DMSO-D6): 0.88 δ(3H, t, J=7 Hz); 1.62 δ(3H, t, J=7 Hz); 1.29 δ(2H, q, J=5.2 Hz); 3.21 δ(2H, q, J=5 Hz); 5.21 δ(2H, s); 5.41 δ(2H, m); 6.51 δ(1H, m); 7.90 δ(11H, d, J=5.4 Hz) m); 7.35 δ(2H, m); 7.90 δ(11H, d, J=5.4 Hz)

$^{13}$C NMR: δ7.3, 13.6, 22.4, 29.8, 72.0, 95.8, 102.4, 124.8, 144.6, 145.3, 156.5, 158.3, 200.1

FAB MS: 403 (M+1)$^+$

Example 7

Preparation 11-Hydroxy-7-Ethyl Camptothecin Using Method B

The procedure for synthesizing 11-hydroxy-7-ethyl camptothecin using method B is as follows: 11-hydroxy camptothecin (3.0 g; 8.2 mmol) is suspended in water (75 ml) and iron (II) sulfate heptahydrate (0.87 g) is added. This solution is cooled in an ice-salt bath and stirred well. Propionaldehyde (12 ml) is introduced, followed by concentrated sulfuric acid (31 ml). Hydrogen peroxide (30%; 8 mole equivalents) is added in a dropwise manner at −10° C. The reaction mixture is then stirred for approximately 2.5 h, during which time the mixture is slowly allowed to warm to room temperature. The dark brown colored reaction mixture is diluted with water (100 ml) and extracted once with ether (100 ml) to remove certain impurities. The aqueous solution is neutralized by the slow addition of solid sodium bicarbonate and extracted with excess 70% chloroform in methanol to recover the products. The combined extracts are dried over anhydrous sodium sulfate, concentrated and flash-chromatographed through a silica gel column using 10% methanol in chloroform as eluant. Final purification is performed by crystallization from 80% methanol in chloroform. Spectral and analytical data match those of an authentic sample.

$^1$H NMR (DMSO-D6): 0.88 δ(3H, t, J=7 Hz); 1.62 δ(3H, t, J=7 Hz); 1.29 δ(2H, q, J=5.2 Hz); 3.21 δ(2H, q, J=5 Hz); 5.21 δ(2H, s); 5.41 δ(2H, m); 6.51 δ(1H, s); 7.25 δ(2H, m); 7.35 δ(2H, m); 7.90 δ(11H, d, J=5.4 Hz)

$^{13}$C NMR: δ7.3, 13.6, 22.4, 29.8, 72.0, 95.8, 102.4, 124.8, 144.6, 145.3, 156.5, 158.3, 200.1

FAB MS: 403 (M+1)$^+$

EXAMPLE 8

Preparation and Administration of Novel Formulations of 7,11-Substituted Camptothecin For injection or infusion into aqueous body fluids, a formulation comprises from about 0.1 to about 2.0 mg of 11,7-HECPT or 11,7-HMCPT dissolved in 1 to 10 parts of dimethylisosorbide in an acidified vehicle comprising between about 10 to about 40 percent of an acceptable alcohol, about 4 to about 10 parts by weight of polyether glycol, and about 1 to about 10 parts of a non-ionic surfactant. Suitable alcohols include dehydrated ethyl alcohol, benzyl alcohol. Suitable polyether glycols, include polyethylene glycol 200, polyethylene glycol 300, propylene glycol. Suitable non-ionic surfactants include polysorbate-80. In a preferred embodiment, the formulation of 11,7-HECPT is supplied as an intravenous injectable in a 5 mg vial comprising a sterile, nonaqueous solution of drug in a vehicle comprising dehydrated ethyl alcohol, benzyl alcohol, citric acid, polyethylene glycol 300, and polysorbate (Tween 80) in acidified medium with a pH of 3 to 4 at a final concentration of 1 mg per 1 to 3 ml.

EXAMPLE 9

Preparation of Novel Formulations of 7,11-Substituted Camptothecin

A second formulation comprises from about 0.1 mg to about 2.0 mg of 11,7-HECPT or 11,7-HMCPT in an acidified vehicle comprising between about 0.1 to 2 parts of an alcohol and about 1 to 10 parts of a non-ionic surfactant. Suitable alcohols include dehydrated ethyl alcohol USP, and benzyl alcohol. Suitable non-ionic surfactants include the polyoxyethylated oils, such as polyoxyethylated vegetable oils, such as castor oil, peanut oil, and olive oil. In a preferred embodiment 0.1 mg to 2 mg 11,7-HECPT is formulated in 1 to 10 pads of dimethylisosorbide, 1 to 10 pads of Cremaphor EL (polyoxyethylated castor oil), 0.1 to 2 pads by weight dehydrated ethyl alcohol USP, and 0.1 to 0.9 parts citric acid to adjust the final pH between 3 to 4.

EXAMPLE 10

Preparation and Administration of Novel Oral Formulations of 7,11-Substituted Camptothecin An oral formulation of 11,7-HECPT or 11,7-HMCPT in soft gelatin capsules (comprised of gelatin/glycerin/sorbitol/purifiers/purified water) containing 1.0 part of 11,7-HECPT or 11,7-HMCPT in 1 to 10 pads of dimethylisosorbide, citric acid 0.1 to 0.5 parts by weight, purified water 1 part by weight, glycerin 1 to 10 parts by weight, and polyethylene glycol 200 to 300 5 to 9 parts by weight, dehydrated ethyl alcohol 0.2 to 2 parts by weight of total solution weight, sodium acetate 0.05 to 0.5 pads by weight, pluronic F-127 poloxamer using 0.05 to 1.0 pads by weight, and taurocholic acid 2 to 10 parts by weight. The soft gelatin capsules may also be composed of any of a number of compounds used for this purpose including, for example, a mixture of gelatin, glycerin, sorbitol, purified water, and parabens.

To prolong the stability and solubility of 11,7-HECPT or 11,7-HMCPT for clinical infusions, the drug may diluted in 5% Dextrose in water (D5W) to a final concentration of 0.001 mg/ml to about 0.1 mg/ml of 11,7-HECPT prior to injection or infusion. Maintaining an acidic pH (3 to 4) in the formulation is particularly important to reduce the slow conversion of 11,7-HECPT lactone to the E-ring-hydrolyzed carboxylate, which occurs at physiological pH. At equilibrium under physiologic pH, the ratio of the open-ring form to lactone increases. Hydrolysis of the lactone ring will be substantially reduced if the drug is kept in an acidic environment.

Some of the unpredictable toxicity reported in earlier clinical trials using sodium camptothecin may have been due to the formation of greater amounts of the lactone form of camptothecin, which is 10-fold more toxic than sodium camptothecin in mice. The lactone form of camptothecin, as in 11,7-HECPT or 11,7-HMCPT, is less water soluble than the carboxylate E-ring form. At the time the early clinical trials were first conducted with camptothecin which was formulated using NaOH, and the significance of maintaining the closed lactone ring for uniform efficacy in treating patients with cancer was not known. The early reported unpredictable clinical toxicities associated with camptothecin administration may have been exacerbated by the NaOH formulation which promotes the formation of the carboxylate form, and by the relative lack of understanding of the significance of the lactone form of camptothecin as it relates to antitumor activity.

The foregoing description of the formulation invention has been directed to particular preferred embodiments in accordance with the requirements of the patent statutes and for purposes of explanation and illustration. Those skilled in the art will recognize that many modifications and changes may be made without departing from the scope and the spirit of the invention.

Initially, patients may be treated in a dose escalation protocol to determine the maximal tolerated dose of the 11,7-HECPT formulation or 11,7-HMCPT formulation. In determining a safe starting dose for 11,7-HECPT, the data from Tables 3 and 4 which illustrate the pharmacology of CPT-11 and SN38 are helpful.

TABLE 3

| | Analysis of AUC and CpMax Ratios of CPT-11: SN38 | | | | |
|---|---|---|---|---|---|
| | AUC CPT-11 (ug × hr/ml) | AUC SN38 (ug × hr/ml) | Ratio AUC CPT-11/SN38 | CpMax CPT-11:SN38 (ug/ml) | CPMax Ratio CPT 11:SN38 |
| Ohe et al. | | | | | |
| 25 mg/m2/d × 5 | 14.1 | 1.08 | 13.0 | 1.178:0.0104 | 11.3:1 |
| 30 mg/m2/d × 5 | 20.5 | 0.96 | 21.3 | 1.500:0.0105 | 14.2:1 |
| 35 mg/m2/d × 5 | 20.5 | 0.91 | 22.5 | 1.538:0.0068 | 22.6:1 |
| 40 mg/m2/d × 5 | 28.5 | 0.86 | 33.1 | 2.043:0.0080 | 25.5:1 |

TABLE 3-continued

| Analysis of AUC and CpMax Ratios of CPT-11: SN38 | | | | |
|---|---|---|---|---|
| AUC CPT-11 (ug × hr/ml) | AUC SN38 (ug × hr/ml) | Ratio AUC CPT-11/SN38 | CpMax CPT-11:SN38 (ug/ml) | CPMax Ratio CPT 11:SN38 |

Rothenberg et al.

| | | | | |
|---|---|---|---|---|
| 50 mg/m2/wk × 4 | 1.13 | 0.0622 | 18.1 | 0.89:0.0264 | 33.7:1 |
| 100 mg/m2/wk × 4 | 2.23 | 0.2148 | 10.4 | 1.29:0.0316 | 98.0:1 |
| 125 mg/m2/wk × 4 | 2.97 | 0.1955 | 15.2 | 1.70:0.0393 | 43.2:1 |
| 150 mg/m2/wk × 4 | 2.81 | 0.1232 | 22.8 | 1.56:0.0367 | 42.5:1 |
| 180 mg/m2/wk × 4 | 3.83 | 0.2328 | 16.5 | 1.97:0.0262 | 75.2:1 |

TABLE 4

Fractional Amounts of Lactone Species of CPT-11 and SN38 as Function of Increasing Single Dose I.V. From Rothenburg et al.

| Dose | CPT-11 AUC Based | SN38 AUC Based | CPT-11 CpMax Based | SN38 CpMax Based |
|---|---|---|---|---|
| 50 mg/m2 | 0.41 | 0.29 | 0.51 | 0.50 |
| 80 mg/m2 | 0.30 | 0.50 | 0.44 | 0.39 |
| 100 mg/m 2 | 0.33 | 0.58 | 0.53 | 0.45 |
| 125 mg/m 2 | 0.39 | 0.43 | 0.55 | 0.41 |
| 150 mg/m 2 | 0.33 | 0.30 | 0.42 | 0.36 |
| 180 mg/m 2 | 0.33 | 0.63 | 0.42 | 0.45 |

Data obtained using the continuous infusion schedule of Ohe et. al. shows that the ratio CPT-11 to SN38 AUCs increases gradually as a function of dose and that this increase is substantially more marked in a single dose study. The data in Table 3 supports the conclusion that conversion of CPT-11 to SN38 is a saturable process which is variable among patients, and further that increases in the dose (e.g., above 30 mg/m$^2$/d) of CPT-11 can result in a decrease in the CpMax of SN38 using a 5 day continuous infusion schedule. Although the factors which are involved in the interpatient variability in these studies is not completely understood, some variability in the pharmacology and metabolic conversion of CPT-11 to SN38 probably exists based on the pharmacologic data reported from several investigators. This variability in the conversion of CPT-11 to SN38 is likely to result in instances of unexpected toxicity or lack of clinical effect by the use of CPT-11. In Table 4, which is based on total AUC and CpMax data, the overall fractional concentration of the lactone species of CPT-11 and SN38 appear to remain fairly constant through a range of doses. 11,7-HECPT, because of its similarity to SN38, is predicted to exhibit antitumor activity when similar concentrations of the former drug are reached in the plasma of patients undergoing treatment.

The administration of 11,7-HECPT or 11,7-HMCPT may be carried out using various schedules and dosages. For example:

1. For intravenous administration, a suitable dose is 0.45 mg to 5.4 mg/m2 per day using a 3 to 5 day continuous infusion schedule every 21 to 30 days or 2.7 to 32.4 mg/m2 given as a 30 to 90 minute infusion every 21 to 30 days;

2. Another schedule involves the administration of 1.29 to 15.5 mg/m2 daily for three consecutive days over 90 minutes intravenously every 21 to 28 days.

3. A suitable oral dose of the drug is 0.5 to 50 mg/m2 per day using the lower dose for a period of 3 to 5 days using divided dosages of administration of two to four times per day.

The parenteral and oral doses can be administered under the supervision of a physician based on gradual escalation of the dosage to achieve the maximum tolerated dose in the individual patient. The oral administration schedule of 11,7-HECPT or 11,7-HMCPT may involve multiple daily doses or single daily doses for one or more consecutive days with the ability of the physician to optimize therapy by reaching the maximum effective antitumor dose that has the least toxicity in the individual patient.

In addition, patients may be given the drug as an inpatient or outpatient using the following exemplary schedules:

1. 2.7 to 32.4 mg/m$^2$ given over 90 minutes I.V. every 21 to 28 days;

2. 1.29 to 15.5 mg/m$^2$ given daily for three consecutive days over 90 minutes I.V. every 21 to 28 days;

3. 1.0 to 20.0 mg/m$^2$ week given once per week× 3consecutive weeks over 90 minutes I.V. with 2 weeks rest after each 3 week cycle for pretreated patients;

4. 2.25 to 24.3 mg/m$^2$ given once per week ×3 consecutive weeks over 90 minutes I.V. for previously untreated patients with 2 weeks rest after each 3 week cycle; and 5. 0.45 to 5.4 mg/m$^2$/d×3 to 5 consecutive days as a continuous intravenous infusion every 21 to 28 days.

In a preferred embodiment, 11,7-HECPT or 11,7-HMCPT is initially given at a lower dose. The dose of 11,7-HECPT or 11,7-HMCPT is then escalated at each successive cycle of treatment until the patient develops side effects which demonstrates individual therapeutic tolerance. The purpose of dose escalation is to safely increases the drug levels to a maximum tolerated dose and should result in increased cytotoxicity and improved antitumor activity.

Dosages can be escalated based on patient tolerance so long as no unacceptable toxicity is observed. Since some clinical drug toxicity is anticipated and acceptable in routine clinical oncology practice, appropriate treatment will be used to prevent toxicity (e.g., nausea and vomiting) or ameliorate signs and symptoms if they are observed (e.g., diarrhea). For example, antiemetics will be administered for nausea and vomiting, antidiarrheals for diarrhea, and antipyretics for fever. Appropriate dosages of steroids/antihistamines will also be used to prevent or ameliorate any anaphylactoid toxicity if an anaphylactoid reaction is observed.

Kaneda's HPLC method and further modifications by Barilero et al. are useful for the measuring quantities of 11,7-HECPT or 11,7-HMCPT in plasma and tissue. In these assays, plasma, serum, and tissue homogenate samples containing 11,7-HECPT or 11,7-HMCPT are immediately diluted 10-fold with 0.1N HCL to give final concentrations of about 100 ng/ml for 11,7 HECPT or 11,7-HMCPT. The diluted plasma or serum samples are applied to a C18 cassette of an automated sample processor Analytichem International, Harbor City, Calif.), which is activated with 1.5 ml of methanol and water. The HPLC apparatus (Model LC-4A; Shimadzu Seisakusho) is linked to the automated sample processor, and a C18 reversed-phase column (LiChrosorb RP-18; 25×0.4 cm; Merck) with an RP-18 precolumn is used for chromatography. The mobile phases consists of CH3CN/water (1/4,v/v) for 11,7-HECPT. The flow rate and column temperature are 2.0 ml/min and 60 degrees Celsius for 11,7-HECPT. A florospectromonitor (Model R-530; Shimadzu Seisakusho) is set at an excitation wavelength of 373 nm and an emission wavelength of 380 nm and a wavelength of 540 nm for 11,7-HECPT. The peak area is integrated by a data processor (Model C-RIBS Chromatopac; Shimadzu Seisakusho). 11,7-HECPT gives retention times of 13.8 min. Calibration curves are established for each determination by 10% mouse serum in 0.1N HCL containing 11,7-HECPT. Validations of 11,7-HECPT determinations will be made by running samples versus real standards. The limit of determination is about 1 to 5 ng for 11,7-HECPT using this assay.

REFERENCES

The following references may facilitate understanding or practice of certain aspects of the present invention. Inclusion of a reference in this list is not intended to and does not constitute an admission that the reference represents prior art with respect to the present invention.

UNITED STATES PATENTS

U.S. Pat. No. 4,545,880 10/85 Miyasaka et al.
U.S. Pat. No. 4,473,692 9/84 Miyasaka et al.
U.S. Pat. No. 4,778,891 10/88 Tagawa et al.
U.S. Pat. No. 5,061,800 10/91 Miyasaka et al.

FOREIGN PATENTS

Al 4-139, 187 05/92 Seigo et al.
AJ63-238,098 10/88 Takashi et al.
AK3-232,888 10/91 Seigo et al.
AL61-85,319 04/86 Teruo et al.

OTHER PUBLICATIONS

Akimoto, K., et al., Selective and Sensitive Determination of Lactone and Hydroxy Acid Forms of Camptothecin and Two Derivatives (CPT-11 and SN-38) by High-Performance Liquid Chromatography with Fluorescence Detection. Journal of Chromatography, 588:165–170, 1991.

Taxotere, Topotecan, and CPT-11: Clinical Trials Confirm Early Promise. Oncology Times, written by O. Baer, pp. 8–10, May 1993.

Barilero et al., Simultaneous Determination of the Camptothecin Analogue CPT11 and Its Active Metabolite SN-38 by High Performance Liquid Chromatography: Application to Plasma Pharmacokinetic Studies in Cancer Patients. J. Chromat. 575:275–280; 1992.

Bates, T. R., et al., Solubilizing Properties of Bile Salt Solutions L I—Effect of Temperature and Bile Salt Concentration On Solubilization of Glutethimide, Griseofulvin and Hexestrol. Journal of Pharmaceutical Sciences, 55:191–199, 1966.

Bates, T. R., et al., Rates of Dissolution of Griseofulvin and Hexestrol in Bile Salt Solutions. Chem. Abstracts 65:8680b, 1966.

Bates, T. R., et al., Solubilizing Properties of Bile Salt Solutions on Glutethimide, Griseofulvin, and Hexestrol. Chem. Abstracts 65:15165a, 1966.

Clavel, M., et al., Phase I Study of the Camptothecin Analogue CPT-11, Administered Daily for 3 Consecutive Days. Proc. Amer. Assoc. Cancer Res. 3:83, 1992.

Creavan, P. J., et al., Plasma Camptothecin (NSC 100880) Levels During a 3-Day Course of Treatment: Relation to Dose and Toxicity. Cancer Chemotherapy Rep. 56:573–578, 1972.

Culine, S., et al., Phase I Study of the Camptothecin Analogue CPT-11, Using a Weekly Schedule. Proc. of Amer. Soc. Clin. Onc. 11:110, 1992.

Eckardt, J. et al., Topoisomerase I Inhibitors: Promising Novel Compounds. Contemporary Oncology, pp. 47–60, 1993.

Ejima, A., et al., Antitumor Agents V.[1)] Synthesis and Antileukemic Activity of E-Ring-Modified (RS)-Camptothecin Analogues. Chem. Pharm. Bull., 40(3) :683–688, March, 1992.

Extra, J. M., et al., Phase I Study of CPT-11, A Camptothecin Analogue, Administered as a Weekly Infusion. Proc. Amer. Assoc. Cancer Res., 3:83, 1992.

Fukuoka, M. et al., A Phase II Study of CPT-11, A New Derivative of Camptothecin, for Previously Untreated Non Small-Cell Lung Cancer. J. Clin. Onc. 10(1):16–20, January, 1992.

Giovanella, B. C. et al., DNA Topoisomerase I—Targeted Chemotherapy of Human Colon Cancer in Xenografts. Science 246:1046–1048, November, 1989.

Gottlieb, J. A., et al., Preliminary Pharmacologic and Clinical Evaluation of Camptothecin Sodium (NSC-100880). Cancer Chemotherapy Reports 54(6):461–470, December, 1970.

Gottlieb, J. A., et al., Treatment of Malignant Melanoma with Camptothecin (NSC 100880). Cancer Chemotherapy Reports 56(1):103–105, February, 1972.

Hsiang et al., Arrest of Replication Forks by Drug-stabilized Topoisomerase I-DNA Cleavable Complexes as a Mechanism of Cell Killing by Camptothecin Analogues. Cancer Res. 49:5077–5082, September, 1989.

Jaxel, C. et at., Structure Activity Study of the Actions of Camptothecin Derivatives on Mammalian Topoisomerase I: Evidence for a Specific Receptor Site and a relation to Antitumor Activity. Cancer Res. 49:1465–1469, March, 1989.

Kaneda, N. et al., Metabolism and Pharmacokinetics of the Camptothecin Analogue CPT-11 in the Mouse. Cancer Research 50:1715–1720, March, 1990.

Kano, Y. et al., Effects of CPT-11 in Combination With Other Anti-Cancer Agents in Culture. Int. J. Cancer 50:604–610, 1992.

Kanzawa F. et al., Role of Carboxylesterase on Metabolism of Camptothecin Analog (CPT-11) in Non-Small Cell Lung Cancer Cell Line PC-7 Cells (Meeting Abstract). Proc. Annual Meet. Am. Assoc. Cancer Res. 33:A2552, 1992.

Kawato, Y. et al., Intracellular Roles of SN-38, a Metabolite of the Camptothecin Derivative CPT-11, in the Antitumor Effect of CPT-11. Cancer Res. 51:4187–4191, August, 1991.

Kawato, Y., et al., Antitumor Activity of a Camptothecin Derivative, CPT-11, Against Human Tumor Xenografts in Nude Mice. Cancer Chemother Pharmacol, 28:192–198, 1991.

Kingsbury, W. D. et al., Synthesis of Water-Soluble (Aminoalkyl) Camptothecin Analogues: Inhibition of Topoisomerase I and Antitumor Activity. J. Meal. Chem. 34:98–107, 1991.

Kunimoto, T. et al., Antitumor Activity of 7-Ethyl-10-[4-(1-piperidino)-1-piperidino]Carbonyloxy-Camptothecin, a Novel Water Soluble Derivative of Camptothecin, Against Murine Tumors. Cancer Res. 47:5944–5947, November, 1987.

Kuhn, J., et al., Pharmacokinetics of Topotecan Following a 30 Min Infusion or 3 Day Continuous Infusion. Proc. Amer. Assoc. Cancer Res., 3:83, 1992.

Malone et al., Desoxycholic Acid Enhancement of Orally Administered Reserpine. Chem. Abstracts 65:14303e; 1966.

Malone, M. H., et al., Desoxycholic Acid Enhancement of Orally Administered Reserpine. Journal of Pharmaceutical Sciences, 55(9):972–974, September, 1966.

Masuda, N. et al., CPT-11: A New Derivative of Camptothecin for the Treatment of Refractory or Relapsed Small-Cell Lung Cancer. J. Clin. Onc. 10(8):1225–1229, August, 1992.

Minisci, F., Novel Applications of Free Radical Reactions in Preparative Organic Chemistry. Synthesis, pps. 1–24, January, 1973.

Moertel, C. G., et al., Phase II Study of Camptothecin (NSC-100880) in the Treatment of Advanced Gastrointestinal Cancer. Cancer Chemotherapy Rep. 56(1):95–101, February, 1972.

Muggia, F. M., et al., Phase I Clinical Trial of Weekly and Daily Treatment With Camptothecin (NSC-100880): Correlation With Preclinical Studies. Cancer Chemotherapy Rep. 56(4):515–521, August, 1972.

Negoro, S. et al., Phase I Study of Weekly Intravenous Infusions of CPT-11, a New Derivative of Camptothecin, in the Treatment of Advanced Non-Small Cell Lung Cancer. JNCI 83 (16): 1164–1168, August, 1991.

Negoro, S. et al., Phase II Study of CPT-11, a New Camptothecin Derivative, in Small Cell Lung Cancer. Proc. Annu. Meet. of Amer. Soc. Clin. Onc. 10:241, August, 1991.

Nicholas, A. W., et al., Plant Antitumor Agents. 29.[1] Synthesis and Biological Activity of Ring D and Ring E Modified Analogues of Camptothecin. J. Med. Chem. 33:978–985, 1990.

Niimi, S. et al., Mechanism of Cross-Resistance to a Camptothecin Analogue (CPT-11) in a Human Ovarian Cancer Cell Line Selected by Cisplatin. Cancer Res. 52:328–333, January, 1992.

Ohe, Y. et al., Phase I Study and Pharmacokinetics of CPT-11 with 5-Day Continuous Infusion. JNCI 84 (12): 972–974, June, 1992.

Ohno, R. et al., An Early Phase II Study of CPT-11: A New Derivative of Camptothecin, for the Treatment of Leukemia and Lymphoma. J. Clin. Onc. 8(11):1907–1912, November, 1990.

Pantazis, P., et al., Cytotoxic Efficacy of 9-Nitrocamptothecin in the Treatment of Human Malignant Melanoma Cells in Vitro[1]. Cancer Research, 54:771–776, February, 1994.

Pommier, Y. et al., Camptothecins: Mechanism of Action and Resistance (Meeting Abstract). Cancer Investigation, Presented at the "Chemotherapy Foundation Symposium X Innovative Cancer Chemotherapy for Tomorrow," page 3–6, 1992.

Pommier, Y., et al., Chapter 9: Mammalian DNA Topoisomerase I and Its Inhibitors. In: Cancer Chemotherapy, Eds. Hickman and Tritton, Publisher, Blackwell Scientific Publications, pp. 214–250, 1993.

Rothenberg, M. L. et al., A Phase I and Pharmacokinetic Trial of CPT-11 in Patients With Refractory Solid Tumors. Proceedings of Amer. Soc. Clin. Onc. 11:113, 1992.

Rothenberg, M. L. et al., Phase I and Pharmacokinetic Trial of Weekly CPT-11. Journal of Clinical Oncology. 11(11):2194–2204, November, 1993.

Rothenberg, M. L. et al., A Phase I and Pharmacokinetic Trial of CPT-11 in Patients with Refractory Solid Tumors. Amer. Soc. Clin. Onc. 11:113, 1992.

Rowinsky, E. et al., Phase I Pharmacologic Study on CPT-11, A Semisynthetic Topoisomerase I-Targeting Agent, on a Single-Dose Schedule (Meeting Abstract). Proc. of Amer. Soc. Clin. Onc. 11:115, 1992.

Rowinsky, E., et al., Phase I and Pharmacologic Studies of Topotecan, A Novel Topoisomerase I Inhibitor Without and With G-CSF. Proc. Amer. Assoc. Cancer Res., 3:83, 1992.

Rowinsky, E. K., et al., Phase I and Pharmacological Study of the Novel Topoisomerase Inhibitor . . . CPT-11 Administered as Ninety-Minute Infusion Every 3 Weeks. Cancer Research, 54:427–436, January, 1994.

Sawada, S. et al., Synthesis and Antitumor Activity of 20 (S)-Camptothecin Derivatives: Carbonate-Linked, Water-Soluble, Derivatives of 7-Ethyl-10-Hydroxycamptothecin. Chem. Pharm. Bull. 39(6):1446–1454, 1991.

Shimada, Y. et al., Phase II Study of CPT-11, New Camptothecin Derivative, in the Patients with Metastatic Colorectal Cancer. Proc. of Amer. Soc. Clin. Onc. 10:135, March, 1991.

Takeuchi, S. et al., Late Phase II Study of CPT-11, A Topoisomerase I Inhibitor, in Advanced Cervical Carcinoma (CC) (Meeting Abstract). Proc. Annu. Meet. of Amer. Soc. Clin. Onc. 11:224, 1992.

Wall, M. E. et al. Plant Anti-Tumor Agents I—The Isolation and Structure of Camptothecin, a Novel Alkaloidal Leulemia and Tumor Inhibitor from Camptotheca Acuminata. J. Amer. Chem. Soc. 88(16):3888–3890, August, 1966.

Westergaard, H., et al., The Mechanism Whereby Bile Acid Mycelles Increase the Rate of Fatty Acid and Cholesterol Uptake Into the Intestinal Mucosal Cell. Journal of Clinical investigation, 58:97–108 July, 1976.

Von Hoff, D. D. Phase I and Pharmacokinetic Trial of Weekly CPT-11. Journal of Clinical Oncology, 11:21942204, 1993.

The foregoing description has been directed to particular embodiments of the invention in accordance with requirements of the Patent Statutes for the purposes of illustration and explanation. It will be apparent, however, to those skilled in this art, that many modifications, changes and variations in the claimed antitumor compositions, solutions, methods of administration of the antitumor compositions set forth will be possible without departing from the scope and spirit of the claimed invention. It is intended that the following claims be interpreted to embrace all such modifications and changes.

What is claimed is:

1. An 11-hydroxy-7-ethyl camptothecin solution consisting essentially of 11-hydroxy-7-ethyl camptothecin dissolved in dimethylisosorbide and a pharmaceutically acceptable acid wherein said acid is an organic carboxylic acid selected from the group consisting of citric acid and taurocholic acid in an admixture with citric acid.

2. The solution of claim 1 wherein said acid is citric acid.

3. An antitumor composition consisting essentially of a solution of 11-hydroxy-7-ethyl camptothecin dissolved in dimethylisosorbide having from 0.1 mg to 15.0 mg 11-hydroxy-7-ethyl camptothecin activity per ml and from 0.01 to 0.9 part by weight of a pharmaceutically acceptable organic carboxylic acid per part by weight of 11-hydroxy-7-ethyl camptothecin, wherein said organic carboxylic acid is selected from the group consisting of citric acid and taurocholic acid in an admixture with citric acid.

4. The antitumor composition of claim 3 wherein said part by weight of a pharmaceutically organic carboxylic acid is from 0.05 to 0.1 part by weight per part by weight of 11-hydroxy-7-ethyl camptothecin.

5. The antitumor composition of claim 4 wherein said acid is citric acid.

6. An antitumor composition consisting essentially of a solution of 11-hydroxy-7-methoxy camptothecin dissolved in dimethylisosorbide having from 0.1 mg to 15.0 mg 11-hydroxy-7-methoxy camptothecin activity per ml and from 0.01 to 0.9 part by weight of a pharmaceutically acceptable organic carboxylic acid per part by weight of 11-hydroxy-7-methoxy camptothecin wherein said organic carboxylic acid is selected from the group consisting of citric acid and taurocholic acid in an admixture with citric acid.

7. The antitumor composition of claim 6 wherein said part by weight of a pharmaceutically organic carboxylic acid is from 0.05 to 0.1 part by weight per part by weight of 11-hydroxy-7-methoxy camptothecin.

8. The antitumor composition of claims 6 wherein said acid is citric acid.

9. An antitumor composition consisting essentially of a solution of 11-hydroxy-7-ethyl camptothecin dissolved in dimethylisosorbide, a pharmaceutically acceptable acid selected from the group consisting of citric acid and taurocholic acid in an admixture with citric acid or a pharmaceutically acceptable salt thereof, polyethylene glycol, glycerin and a lower alcohol selected from the group consisting of ethyl alcohol and ethyl alcohol in an admixture with benzyl alcohol.

10. The antitumor composition of claim 9 wherein said solution has for each part by weight of 11-hydroxy-7-ethyl camptothecin, 1 to 10 parts by weight of dimethylisosorbide, 0.005 to 0.5 parts by weight of a pharmaceutically acceptable acid selected from the group consisting of citric acid and 1 to 10 parts by weight of taurocholic acid in an admixture with citric acid or a pharmaceutically acceptable salt thereof, and 1 to 10 parts by weight of polyethylene glycol.

11. The antitumor composition of claim 9 wherein said carboxylic acid is citric acid.

12. An antitumor composition consisting essentially of a solution of 11-hydroxy-7-methoxy camptothecin dissolved in dimethylisosorbide, a pharmaceutically acceptable acid selected from the group consisting of citric acid and taurocholic acid in an admixture with citric acid or a pharmaceutically acceptable salt thereof, polyethylene glycol, glycerin and a lower alcohol selected from the group consisting of ethyl alcohol and ethyl alcohol in an admixture with benzyl alcohol.

13. The antitumor composition of claim 12 wherein said solution has for each part by weight of 11-hydroxy-7-methoxy camptothecin, 1 to 10 parts by weight of dimethylisosorbide, 0.005 to 0.5 parts by weight of a pharmaceutically acceptable acid selected from the group consisting of citric acid and 1 to 10 parts by weight of taurocholic acid in an admixture with citric acid or a pharmaceutically acceptable salt thereof, and 1 to 10 parts by weight of polyethylene glycol.

14. The antitumor composition of claim 12 wherein said carboxylic acid is citric acid.

15. An antitumor composition consisting essentially of a solution of 11-hydroxy-7-ethyl camptothecin dissolved in dimethylisosorbide, a pharmaceutically acceptable acid selected from the group consisting of citric acid, and taurocholic acid in an admixture with citric acid, or a pharmaceutically acceptable salt thereof, polyethylene glycol, ethanol, glycerin, and a buffer.

16. The antitumor composition of claim 15 wherein said solution has for each part by weight of 11-hydroxy-7-ethyl camptothecin, 1 to 10 parts by weight of dimethylisosorbide, 0.005 to 0.5 parts by weight of a pharmaceutically acceptable acid selected from the group consisting of citric acid and 1 to 10 parts by weight of taurocholic acid in an admixture with citric acid or a pharmaceutically acceptable salt thereof, 1 to 10 parts by weight of polyethylene glycol, 0.1 to 2 parts by weight of glycerin, 0.1 to 2 parts by weight of ethanol, and 0.005 to 0.5 parts of a buffer.

17. An antitumor composition consisting essentially of a solution 11-hydroxy-7-methoxy camptothecin dissolved in dimethylisosorbide, a pharmaceutically acceptable acid selected from the group consisting of citric acid, and taurocholic acid in an admixture with citric acid, or a pharmaceutically acceptable salt thereof, polyethylene glycol, ethanol, glycerin, and a buffer.

18. The antitumor composition of claim 17 wherein said solution has for each part by weight of 11-hydroxy 7-methoxy camptothecin, 1 to 10 parts by weight of dimethylisosorbide, 0.005 to 0.5 parts by weight of a pharmaceutically acceptable acid selected from the group consisting of citric acid and 1 10 parts by weight of taurocholic acid in an admixture with citric acid or a pharmaceutically acceptable salt thereof, 1 to 10 parts by weight of polyethylene glycol, 0.1 to 2 parts by weight of glycerin, 0.1 to 2 parts by weight of ethanol, and 0.005 to 0.5 parts of a buffer.

19. The antitumor composition of claims 9, 12, 15, and 17 wherein said polyethylene glycol has a molecular weight of 300.

20. An antitumor composition consisting essentially of a solution of 11-hydroxy-7-ethyl camptothecin dissolved in dimethylisosorbide, in the presence of a pharmaceutically acceptable acid selected from the group consisting of citric acid and taurocholic acid in an admixture with citric acid, a lower alcohol, polyethylene glycol, and a surfactant.

21. The antitumor composition of claim 20 wherein said pharmaceutically acceptable acid is citric acid, wherein said polyethylene glycol has a molecular weight of 300, wherein said lower alcohol is ethanol and wherein said surfactant is polysorbate-80.

22. An antitumor composition consisting essentially of a solution of 0.1 mg to 15.0 mg of 11-hydroxy-7-ethyl camptothecin dissolved in 1 to 10 parts of dimethylisosorbide, in the presence of 0.1 to 0.5 parts of a pharmaceutically acceptable organic carboxylic acid selected from the group consisting of citric acid and taurocholic acid in an admixture with citric acid, wherein said solution further has 5 to 9 parts by weight of polyethylene glycol, 0.1 to 2.0 parts of a pharmaceutically acceptable alcohol, and 1 to 10 parts of a non-ionic surfactant.

23. An antitumor composition consisting essentially of a solution of 11-hydroxy-7-methoxy camptothecin dissolved in dimethylisosorbide in the presence of a pharmaceutically acceptable acid selected from the group consisting of citric acid and taurocholic acid in an admixture with citric acid, a lower alcohol, polyethylene glycol, and a surfactant.

24. The antitumor composition of claim 23 wherein said pharmaceutically acceptable organic acid is citric acid, wherein said polyethylene glycol has a molecular weight of 300, wherein said lower alcohol is ethanol and wherein said surfactant is polysorbate-80.

25. An antitumor composition consisting essentially of a solution of 0.1 mg to 15.0 mg of 11-hydroxy-7-methoxy camptothecin dissolved in 1 to 10 parts of dimethylisosorbide in the presence of 0.1 to 0.5 parts of a pharmaceutically acceptable organic carboxylic acid selected from the group consisting of citric acid and taurocholic acid in an admixture with citric acid, wherein said solution further has 5 to 9 parts by weight of polyethylene glycol, 0.1 to 2.0 parts of a pharmaceutically acceptable alcohol, and 1 to 10 parts of a non-ionic surfactant.

26. The antitumor composition of claims 22 or 25 wherein said acid is citric acid, wherein said polyethylene glycol has a molecular weight of 300, wherein said alcohol is ethanol and wherein said surfactant is polysorbate-80.

27. An antitumor composition consisting essentially of a solution of 0.1 mg to 15.0 mg of 11-hydroxy-7-ethyl camptothecin dissolved in 1 to 10 parts of dimethylisosorbide in the presence of 0.1 to 0.5 parts of a pharmaceutically acceptable organic carboxylic acid selected from the group consisting of citric acid and taurocholic acid in an admixture with citric acid, wherein said solution further has 0.1 to 2.0 parts of a pharmaceutically acceptable alcohol, and 1 to 10 parts of a non-ionic surfactant.

28. The antitumor composition of claim 27 wherein said acid is citric acid, wherein said alcohol is ethanol, and wherein said non-ionic surfactant is polyoxyethylated castor oil.

29. An antitumor composition consisting essentially of a solution of 0.1 mg to 15.0 mg of 11-hydroxy-7-methoxy camptothecin dissolved in 1 to 10 parts of dimethylisosorbide in the presence of 0.1 to 0.5 parts of a pharmaceutically acceptable organic carboxylic acid selected from the group consisting of citric acid and taurocholic acid in an admixture with citric acid, wherein said solution further has 0.1 to 2.0 parts of a pharmaceutically acceptable alcohol, and 1 to 10 parts of a non-ionic surfactant.

30. The antitumor composition of claim 29 wherein said acid is citric acid, wherein said alcohol is ethanol, and wherein said non-ionic surfactant is polyoxyethylated castor oil.

31. An antitumor composition consisting essentially of a solution of 0.1 mg to 15.0 mg of 11-hydroxy-7-ethyl camptothecin dissolved in 1 to 10 parts of dimethylisosorbide, wherein said solution further has 1 to 10 parts polyoxyethylated castor oil, 0.1 to 2 parts by weight dehydrated ethyl alcohol USP, and 0.1 to 0.9 parts citric acid.

32. An antitumor composition consisting essentially of a solution of 0.1 mg to 15.0 mg of 11-hydroxy-7-methoxy camptothecin dissolved in 1 to 10 parts of dimethylisosorbide, wherein said solution further has 1 to 10 parts polyoxyethylated castor oil, 0.1 to 2 parts by weight dehydrated ethyl alcohol USP, and 0.1 to 0.9 parts citric acid.

33. An 11-hydroxy 7-methoxy camptothecin solution consisting essentially of 11-hydroxy-7-methoxy camptothecin dissolved in dimethylisosorbide and a pharmaceutically acceptable acid wherein said acid is an organic carboxylic acid selected from the group consisting of citric acid and taurocholic acid in an admixture with citric acid.

34. The solution of claim 1 or 33 wherein said solution contains from 0.1 mg to 5.0 mg activity of said compound per ml of solution.

35. The solution of claim 33 wherein said acid is citric acid.

36. The solution of claim 33 wherein said solution is sterilized and prepared for oral, intrapleural, intrathecal, intracisternal, intravesicular, intraperitoneal, subcutaneous, topical or parenteral administration to a patient with cancer.

37. The solution of claim 1 wherein said solution is sterilized and prepared for oral, intrapleural, intrathecal, intracisternal, intravesicular, intraperitoneal, subcutaneous, topical or parenteral administration to a patient with cancer.

38. The solution of claims 1, 3, 6, 9, 12, 15, 17, 20, 22, 23, 25, 27, 29, 31, 32, and 33 wherein said solution is encapsulated within a hard gelatin capsule.

39. The solution of claims 1, 3, 6, 9, 12, 15, 17, 20, 22, 23, 25, 27, 29, 31, 32, and 33 wherein said solution is encapsulated within a soft gelatin capsule.

40. The antitumor composition of claims 9, 12, 15, and 17 which further contain a non-ionic surfactant.

41. The antitumor composition of claim 40 wherein said surfactant is a poloxamer.

42. The antitumor composition of claim 41 wherein said poloxamer is pluronic F-127 or poloxamer 407.

* * * * *